United States Patent
Ts'O et al.

(10) Patent No.: US 7,262,177 B2
(45) Date of Patent: *Aug. 28, 2007

(54) CONJUGATES OF GLYCOSYLATED/GALACTOSYLATED PEPTIDE, BIFUNCTIONAL LINKER, AND NUCLEOTIDIC MONOMERS/POLYMERS, AND RELATED COMPOSITIONS AND METHODS OF USE

(75) Inventors: Paul O. P. Ts'O, Ellicott City, MD (US); Robert Duff, York, PA (US); Scott Deamond, Baltimore, MD (US)

(73) Assignee: Cell Works Therapeutics, Inc., Abingdon, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/152,135

(22) Filed: Jun. 14, 2005

(65) Prior Publication Data

US 2005/0250679 A1    Nov. 10, 2005

Related U.S. Application Data

(63) Continuation of application No. 09/998,497, filed on Nov. 30, 2001, now Pat. No. 6,906,182.

(60) Provisional application No. 60/250,139, filed on Dec. 1, 2000.

(51) Int. Cl.
   *A01N 43/04*    (2006.01)
   *A61K 31/715*   (2006.01)
   *A01N 37/18*    (2006.01)
   *A61K 38/00*    (2006.01)

(52) U.S. Cl. .................... 514/50; 514/2; 514/8; 514/49; 530/391.9; 530/391.7; 530/395; 530/397; 530/322; 536/23.1

(58) Field of Classification Search ................ 530/322, 530/391.9, 391.7, 395, 397; 514/8, 49, 50, 514/2; 536/23.1
See application file for complete search history.

(56) References Cited

U.S. PATENT DOCUMENTS

| | | | |
|---|---|---|---|
| 4,415,732 A | 11/1983 | Caruthers et al. | |
| 4,671,958 A | 6/1987 | Rodwell et al. | |
| 4,680,338 A | 7/1987 | Sundoro | |
| 4,725,677 A | 2/1988 | Köster et al. | |
| 4,770,183 A | 9/1988 | Groman et al. | |
| 4,827,945 A | 5/1989 | Groman et al. | |
| 4,952,394 A | 8/1990 | Senter | |
| 4,975,278 A | 12/1990 | Senter et al. | |
| 5,006,652 A | 4/1991 | Cullinan et al. | |
| 5,010,176 A | 4/1991 | Barton | |
| 5,017,693 A | 5/1991 | Hylarides et al. | |
| 5,028,697 A | 7/1991 | Johnson et al. | |
| 5,087,616 A | 2/1992 | Myers et al. | |
| 5,094,849 A | 3/1992 | Cullinan et al. | |
| 5,116,944 A | 5/1992 | Sivam et al. | |
| 5,122,368 A | 6/1992 | Greenfield et al. | |
| 5,141,648 A | 8/1992 | Hylarides et al. | |
| 5,141,739 A | 8/1992 | Jung et al. | |
| 5,144,012 A | 9/1992 | Johnson et al. | |
| 5,149,794 A | 9/1992 | Yatvin et al. | |
| 5,169,933 A | 12/1992 | Anderson et al. | |
| 5,248,492 A | 9/1993 | Groman et al. | |
| 5,280,113 A | 1/1994 | Rademacher et al. | |
| 5,284,646 A | 2/1994 | Menz et al. | |
| 5,308,604 A | 5/1994 | Sinn et al. | |
| 5,336,506 A | 8/1994 | Josephson et al. | |
| 5,342,607 A | 8/1994 | Josephson | |
| 5,352,432 A | 10/1994 | Menz et al. | |
| 5,393,737 A | 2/1995 | Mayers et al. | |
| 5,433,955 A | 7/1995 | Bredehorst et al. | |
| 5,457,187 A | 10/1995 | Gmeiner et al. | |
| 5,478,576 A | 12/1995 | Jung et al. | |
| 5,490,991 A | 2/1996 | Enriquez et al. | |
| 5,492,821 A | 2/1996 | Callstrom et al. | |
| 5,495,006 A | 2/1996 | Climie et al. | |

(Continued)

FOREIGN PATENT DOCUMENTS

EP    0 884 327 B1    3/2001

(Continued)

OTHER PUBLICATIONS

Agrawal et al., "Oligodeoxynucleoside Phosphoramidates and Phosphorothioates as Inhibitors of Human Immunodeficiency Virus," *Proc. Natl. Acad. Sci. USA*, 85(19):7079-7083 (1988) Abstract Only.

Agris et al., "Inhibition of Vesicular Stomatitis Virus Protein Synthesis and Infection by Sequence-Specific Oligodeoxyribonucleoside Methylphosphonates," *Biochemistry*, 25:6268-6275 (1986).

Akhtar et al., "Stability of Antisense DNA Oligodeoxynucleotide Analogs in Cellular Extracts and Sera," *Life Science*, 49: 1793-1801, (1991).

(Continued)

*Primary Examiner*—Patrick Lewis
(74) *Attorney, Agent, or Firm*—Fish & Richardson P.C.

(57) ABSTRACT

A conjugate of formula A-L-P, in which:
   A represents a glycosylated/galactosylated peptide that binds to a cell-surface receptor,
   L represents a bifunctional linker, which does not comprise a naturally occurring amino acid and is covalently bonded to A and P in a regiospecific manner, and
   P represents a monomer, homopolymer or heteropolymer comprising at least one nucleotide or an analogue thereof, which inhibits the intracellular biosynthesis of nucleotides or nucleic acids in a sequence-independent manner,
wherein either or both of the covalent bond between A and L and the covalent bond between L and P can be cleaved intracellularly; a composition comprising such a conjugate; and a method of inhibiting abnormal cellular proliferation in a mammal; and a method of inhibiting replication of a virus in a mammal.

3 Claims, 15 Drawing Sheets

U.S. PATENT DOCUMENTS

| | | | |
|---|---|---|---|
| 5,554,386 | A | 9/1996 | Groman et al. |
| 5,563,250 | A | 10/1996 | Hylarides et al. |
| 5,574,142 | A | 11/1996 | Meyer, Jr. et al. |
| 5,589,334 | A | 12/1996 | Coulie et al. |
| 5,612,474 | A | 3/1997 | Patel |
| 5,614,505 | A | 3/1997 | Gmeiner et al. |
| 5,622,929 | A | 4/1997 | Willner et al. |
| 5,635,382 | A | 6/1997 | Low et al. |
| 5,639,633 | A | 6/1997 | Callstrom et al. |
| 5,646,298 | A | 7/1997 | Powell |
| 5,663,321 | A | 9/1997 | Gmeiner et al. |
| 5,665,358 | A | 9/1997 | Barton et al. |
| 5,679,323 | A | 10/1997 | Menz et al. |
| 5,681,811 | A | 10/1997 | Ekwuribe |
| 5,700,921 | A | 12/1997 | Westling et al. |
| 5,700,922 | A | 12/1997 | Cook |
| 5,741,900 | A | 4/1998 | Gmeiner et al. |
| 5,773,435 | A | 6/1998 | Kadow et al. |
| 5,789,248 | A | 8/1998 | Fodstad et al. |
| 5,840,674 | A | 11/1998 | Yatvin et al. |
| 5,846,728 | A | 12/1998 | Haralambidis et al. |
| 5,880,097 | A | 3/1999 | Lyttle et al. |
| 5,880,270 | A | 3/1999 | Berninger et al. |
| 5,929,049 | A | 7/1999 | Singh et al. |
| 5,981,507 | A | 11/1999 | Josephson et al. |
| 5,994,517 | A | 11/1999 | Ts'o et al. |
| 6,005,094 | A | 12/1999 | Simon et al. |
| 6,005,098 | A | 12/1999 | Hattori et al. |
| 6,030,997 | A | 2/2000 | Eliat et al. |
| 6,037,329 | A | 3/2000 | Baird et al. |
| 6,063,604 | A | 5/2000 | Wick et al. |
| 6,077,837 | A | 6/2000 | Kozak |
| 6,114,520 | A | 9/2000 | Hattori et al. |
| 6,187,335 | B1 | 2/2001 | Brey et al. |
| 6,342,485 | B1 | 1/2002 | Gmeiner et al. ............ 514/44 |

FOREIGN PATENT DOCUMENTS

| | | |
|---|---|---|
| WO | 97/20563 | 6/1997 |
| WO | 00/69473 | 11/2000 |
| WO | 01/32623 A1 | 5/2001 |

OTHER PUBLICATIONS

Alt et al., "Core Specific Antisense Phosphorothioate Oligodeoxynucleotides as Potent and Specific Inhibitors of Hepatitis C Viral Translation," *Arch. Virol*, 142:589-599 (1997).

Andersson, "Reduction and Reoxidation of the Disulfide Bonds of Bovine Serum Albumin," *Archives of Biochemistry and Biophysics*, 133:277-285 (1969).

Asayama et al., "Synthesis Of Novel Polyampholyte Comb-Type Copolymers Consisting Of A Poly (L-Lysine) Backbone And Hyaluronic Acid Side Changes For A DNA Carrier," *Bioconjugate Chem.*, 9: 476-481 (1998).

Bider et al., "Ligand-induced Endocytosis of the Asialoglycoprotein Receptor: Evidence for Heterogeneity in Subunit Oligomerization," *FEBS Lett.* 434; 37-41 (1998).

Biessen et al., "Cholesterol Derivative of a New Triantenarry Cluster Galactoside Directs Low- and High-density Lipoproteins to the Parenchymal Liver Cell," *Biochem. J.*, 302: 283-289 (1994).

Biessen et al., "Synthesis of Cluster Galactosides with High Affinity for the Hepatic Asialoglycoprotein Receptor," *J. Med. Chem.*, 38: 1538-1546 (1995).

Biessen et al., "Cholesterol Derivative of a New Triantenarry Cluster Galactoside Lowers Serum Cholesterol Levels and Enhances Secretion of Bile Acids in the Rat," *Circulation*, 91: 1847-1854 (1995).

Biessen et al., "Targeted Delivery of Oligonucleotides to Parenchymal Liver Cells in Vivo," *Biochem. J.*, 340: 783-792 (1999).

Biessen et al., "Targeted Delivery of Antisense Oligonucleotides to Parenchymal Liver Cells in Vivo," *Methods in Enzymology*, 314: 324-342 (1999).

Biessen et al., "Novel Hepatotrophic Prodrugs of the Antiviral Nucleoside 9-(2-Phosphonylmethoxyethyl) Adenine with Improved Pharmacokinetics and Antiviral Activity," *FASEB J.*, 14: 1784-1792 (Sep. 2000).

Bonfils et al., "Drug targeting: Synthesis and Endocytosis of Oligonucleotide-Neoglycoprotein Conjugates," *Nucleic Acids Res.*, 20(17): 4621-4629 (1992).

Boussif et al., "A Versatile Vector for Gene and Oligonucleotide Transfer into Cells in Culture and in Vivo: Polyethylenimine," *Proc. Natl. Acad. Sci. USA*, 92: 7297-7301 (1995).

Breton et al., "Production of Macrophage-derived Cytotoxic Factor by N-[3-[(Carbamoylmethyl)thio]propionylated] Neoglycoproteins," *Bioconjugate Chemistry*, 2: 16-18 (1991).

Bruix, "Treatment of Hepatocellular Carcinoma," *Hepatology*, 25: 259-262 (1997).

Bunnell et al., "Targeted Delivery of Antisense Oligonucleotides by Molecular Conjugates," *Somatic Cell and Molecular Genetics*, 18(6): 559-569 (1992).

Caruthers, "Chemical Synthesis of DNA and DNA Analogues," *Acc. Chem. Res*. 24: 278-284 (1991).

Cattaneo-Pangrazzi et al., "Cell-cycle Arrest and p53-independent Induction of Apoptosis in Vitro by the New Anticancer Drugs 5-FdUrd-P-FdCydOct and dCydPam-P-FdUrd in DU-145 Human Prostate Cancer Cells," *J. Cancer Res. Clin. Oncol.*, 126: 247-256 (May 2000).

Cheng et al., "Characterization of an Antineoplastic Glucuronide Prodrug," *Biochem. Pharmacol.*, 58: 325-328 (1999).

Chipowsky et al., "Synthesis of 1-thioaldosides Having an Amino Group at the Aclycon Terminal," *Carbohydrate Res.*, 31: 339-346 (1973).

Chu et al., "Presentation of Ligands on Hydroxylapatite," *Bioconjugate Chem.*, 8: 103-105 (1997).

Czerwinski et al., "Cytotoxic Agents Directed to Peptide Hormone Receptors: Defining the Requirements for a Successful Drug," *Proc. Natl. Acad. Sci. USA*, 95: 11520-11525 (1998).

Duff et al., "Intrabody Tissue-Specific Delivery of Antisense Conjugates in Animals: Ligand-Lihnker-Antisense Oligomer Conjugates," *Methods in Enzymology*, 313: 297-321 (1999).

Eichler et al., "Studies on the Uptake of Low Molecular Weight Monomeric Tris-galactosyl Conjugates by the Rat Liver," *Biochem. Pharmacol.*, 44(11):2117-2122 (1992).

Findeis et al., "Ligand-Based Carrier Systems for Delivery of DNA to Hepatocytes," *Methods in Enzymology*, 247: 341-351 (1994).

Findeis, "Stepwise Synthesis of a GalNAc-Containing Cluster Glycoside Ligand of the Asialoglycoprotein Receptor," *Int. J. Peptide Protein Res.*, 43: 477-485 (1994).

Franssen et al., "Hepatic and Intrahepatic Targeting of an Anti-Inflammatory Agent with Human Serum Albumin and Neoglycoproteins as Carrier Molecules," *Biochem. Pharmacol.*, 45(6): 1215-1226 (1993).

Gupta et al., "Synthesis of Neoglycopeptides and Analyses of their Biodistribution In Vivo to Identify Tissue Specific Uptake and Novel Putative Membrane Lectins," *Glycoconjugate J.*, 11: 558-571 (1994).

Hangeland et al., "Cell-type Specific and Ligand Specific Enhancement of Cellular Uptake of Oligodeoxynucleoside Methylphosphonates Covalently Linked with a Neoglycopeptide, YEE(ah-GalNAc)$_3$," *Bioconjugate Chem.*, 6: 695-701 (1995).

Hardy et al., "Different Modes of Ligand Binding to the Hepatic Galactose/N-Acetylgalactosamine Lectin on the Surface of Rabbit Hepatocytes," *Biochem.*, 24: 22-28 (1985).

Huwyler et al., "Receptor Mediated Delivery of Daunomycin Using Immunoliposomes: Pharmacokinetics and Tissue Distribution in the Rat," *JPET*, 282: 1541-1546 (1997).

Krieg et al., "Modification of Antisense Phosphodiester Oligodeoxynucleotides by a 5' Cholesteryl Moiety Increases Cellular Association and Improves Efficacy," *Proc. Natl. Acad. Sci. USA*, 90: 1048-1052 (1993).

Kuo et al., "Novel Systems for Controlled Delivery of Macromolecules," *Crit. Rev. Eukaryotic Gene Express.*, 6(1): 59-73 (1996).

Lemaitre et al., "Specific Antiviral Activity of a Poly(L-Lysine)-conjugated Oligodeoxyribonucleotide Sequence Complementary to Vesicular Stomatitis Virus N Protein mRNA Initiation Site," *Proc. Natl. Acad. Sci. USA*, 84: 648-652 (1987).

Lee, "Synthesis of Some Cluster Glycosides Suitable for Attachment to Proteins or Solid Matrices," *Carbohydrate Research*, 67: 509-514 (1978).

Lee et al., "New Synthetic Cluster Ligands for Galactose/N-Acetylgalactosamine-Specific Lectin of Mammalian Liver," *Biochem.*, 23: 4255-4261 (1984).

Lee et al., "Synthesis of 6'-Aminohexyl 2-Acetamido-2-Deoxy-D-Galactoside Isomers and a Unique Isomerization Catalyzed by Ion Exchange Resin," *J. Carbohydrate Chemistry*, 5(3): 343-357 (1986).

Lee et al., "Binding Characteristics of N-Acetylglucosamine-Specific Lectin of the Isolated Chicken Hepatocytes: Similarities to Mammalian Hepatic Galactose/N-Acetylgalactosamine-Specific Lectin," *Biochem.*, 28: 8351-8358 (1989).

Lee, "Binding Modes of Mammalian Hepatic Gal/Ca1NAc Receptors," *Ciba Found. Symp.*, 145: 80-95 (1989).

Lee et al., "Ligand Structural Requirements for Recognition and Binding by the Hepatic Asialoglycoprotein Receptor," *Targeted Diagn. Ther.*, 4: 65-86 (1991).

Lee, "Biochemistry of Carbohydrate-Protein Interaction," *FASEB J.*, 6: 3193-3200 (1992).

Lee et al., "Facile Synthesis of a High-Affinity Ligand for Mammalian Hepatic Lectin Containing Three Terminal N-Acetylgalactosamine Residues," *Bioconjug. Chem.*, 8(5): 762-765 (1997).

Lee-Young et al., "Neocglycoconjugates: Preparation and Application," *Acad. Press, Inc.*, 511-537 (1994).

Levis et al., "Cellular Uptake of Oligodeoxyribonucleoside Methylphosphonates," *Antisense Research and Development*, 5: 251-259 (1995).

Lu et al., "Antisense DNA Delivery in Vivo: Liver Targeting by Receptor-Mediated Uptake," *J. Nucl. Med.*, 35: 269-275 (1994).

Marshall et al., "Inhibition of Human Immunodeficiency Virus Activity by Phosphorodithioate Oligodeoxycytidine," *Proc. Natl. Acad. Sci. USA*, 89: 6265-6269 (1992).

Martinez-Fong et al., "Nonenzymatic Glycosylation of Poly-L-lysine: A New Tool for Targeted Gene Delivery," *Hepatology*, 20(6): 1602-1608 (1994).

Merwin et al., "Targeted Delivery of DNA using YEE(GalNAcAH)$_3$, A Synthetic Glycopeptide Ligand for the Asialoglycoprotein Receptor," *Bioconjugate Chem.* 5: 612-620 (1994).

Mier et al., "Preparation and Evaluation of Tumor-Targeting Peptide-Oligonucleotide Conjugates," *Bioconjugate Chem.*, 11: 855-860 (Nov.-Dec. 2000).

Milligan et al., "Current Concepts in Antisense Drug Design," *Journal of Medicinal Chemistry*, 36(14): 1923-1937 (1993).

O'Connor et al., "Biological Activity of a Novel Rationally Designed Lipophilic Thymidylate Synthase Inhibitor," *Cancer Chemother. Pharmacol.*, 34: 225-229 (1994).

Ozaki et al., "The Differences in Structural Specificity for Recognition and Binding Between Asialoglycoprotein Receptors of Liver and Macrophages," *Glycoconjugate Journal*, 12: 268-274 (1995).

Périgaud et al., "Nucleoside Analogues as Chemotherapeutic Agents: A Review," *Nucleosides and Nucleotides*, 11(2-4): 903-945 (1992).

Plank et al., "Gene Transfer into Hepatocytes Using Asialoglycoprotein Receptor Mediate Endocytosis of DNA Complexed with an Artificial Tetra-Antennary Galactose Ligand," *Bioconjugate Chem.*, 3: 533-539 (1992).

Ranade, "Drug Delivery Systems: 3A. Role of Polymers in Drug Delivery," *J. Clin. Pharmacol.*, 30: 10-23 (1990).

Rice et al., "Defined Geometry of Binding between Triantennary Glycopeptide and the Asialoglycoprotein DNA of Rat Heptocytes," *J. Biol. Chem.*, 265(30): 18429-18434 (1990).

Rice et al., "Interterminal Distance and Flexibility of a Triantennary Glycopeptide as Measured by Resonance Energy Transfer," *Biochem.*, 30: 6646-6655 (1991).

Richardson et al., "Potential of Low Molecular Mass Chitosan as a DNA Delivery System: Biocompatibility, Body Distribution and Ability to Complex and Protect DNA," *Intl. J. Pharm.*, 178: 231-243 (1999).

Robinson et al., "Bioadhesive Polymers for Controlled Drug Delivery," *Annals New York Academy of Sciences*, 507: 307-314 (1987).

Rohlff et al., "A Novel, Orally Administered Nucleoside Analogue, OGT 719, Inhibits the Liver Invasive Growth of a Human Colorectal Tumor, C170HM2," *Cancer Res.*, 59: 1268-1272 (1999).

Schwarz et al., "Preparation, Antibacterial Effects and Enzymatic Degradation of 5-Fluorouracil Nucleosides," *Collection Czechoslov. Chem. Commun.*, 45: 3217-3230 (1980).

Sett et al., "Macrophage-Directed Delivery of Doxorubicin Conjugated to Neoglyoprotein Using Leishmaniasis as the Model Disease," *J. Infectious Diseases*, 168: 994-999 (1993).

Shaw et al., "Modified Deoxyoligonucleotides Stable to Exonuclease Degradation in Serum," *Nuc. Acids Res.*, 19(4): 747-750 (1991).

Smith, "Amphipathic Enzyme-Polymer Conjugates," *Nature*, 262: 519-520 (1976).

Smith et al., "Oligonucleotide Labeling Methods 4 Difrect Labeling Reagents with a Novel, Non-Nucleosidic, Chirally Defined 2-Deoxy-$\beta$-D-Ribosyl Backbone," *Nucleosides & Nucleotides*, 15(10):1581-1594 (1996).

Stein et al., "Oligodeoxynucleotides as Inhibitors of Gene Expression: A Review," *Cancer Res.*, 48:2659-2668 (1988).

Takakura et al., "Drug Delivery Systems for Macromolecular Drugs," *Yakugaku Zasshi*, 116(7):519-532 (1996), Abstract Only.

Townsend, et al., "Binding of N-Linked Bovine Fetuin Glycopeptides to Isolated Rabbit Hepatocytes Gal/GalNAc Hepatic Lectin Discrimination between Gal$\beta$(1,4)GlcNAc and Gal$\beta$(1,3)GlcNAc in a Triantennary Structure," *Biochem.*, 25: 5716-5725 (1986).

Theré et al., "The Asialoglycoprotein Receptor in Human Hepatocellular Carcinomas: Its Expression on Proliferating Cells," *British J. Cancer*, 81(3): 404-408 (1999).

Ulbrich et al., "Synthesis of Biodegradable Polymers for Controlled Drug Release," *Annals New York Acad. Sci.*, 831: 47-56 (1997).

Van Berkel et al., "The Effect of a Water-Soluble Tris-Galactoside-Terminated Cholesterol Dervative on the Fate of Low Density Lipoproteins and Liposomes," *J.Biol. Chem.*, 260(5): 2694-2699 (1985).

Wadhwa et al., "Targeted Gene Delivery with a Low Molecular Weight Glycopeptide Carrier," *Bioconjugate Chem.*, 6:283-291 (1995).

Wadhwa et al., "Receptor Mediated Glycotargeting," *J. Drug Targeting*, 3: 111-127 (1995).

Waldner et al., "Hydrophobic Effects in Duplexes with Modified Oligonucleotide Backbones and RNA," *Bioorganic & Medicinal Chemistry Letters*, 6(19): 2363-2366 (1996).

Weigel et al., "Preparation of 6-Aminohexyl D-Aldopyranosides," *Carbohydrate Res.*, 70: 83-91 (1979).

Wolfrum et al., "Fatty acids and Hypolipidemic Drugs Rgulate Peroxisome Proliferator-activated Receptors Alpha- and Gamma-mediated Gene Expression Via Liver Fatty Acid Binding Protein: A signaling Path to the Nucleus," *Proc. Natl. Acad. Sci. USA*, 98(5): 2323-2328 (Feb. 2001).

Wong et al., "Synthesis of D-galactosamine Derivatives and Binding Studies Using Isolated Rat Hepatocytes," *Carbohydrate Res.* 170: 27-46 (1987).

Wu et al., "Targeted Delivery and Expression of Foreign Genes in Hepatocytes," *Targeted Diagnosis & Therapy*, 4: 127-149 (1991).

Zaia et al., "Inhibition of Human Immunodeficiency Virus by Using an Oligonucleoside Methylphosphonate Targeted to the *tat*-3 Gene," *J. Virol.*, 62(10): 3914-3917 (1988).

Desmoulin et al. "Metabolism of a novel nucleoside analogue, OGT 719, in the isolated perfused rat liver model, in rats . . . " *Xenobiotica* 33(3):289-303, 2003.

Di Stefano et al., "Conugation of 5-fluoro-2'-deoxyuridine with lactosaminated poly-l-lysine to reduce extrahepatic toxicity . . . " Ital. J. of Gastroenterol Hepatol. 30:173-177, 1998.

Rohlff et al., "Hepatocyte-activated glycol-conjugated 5-FU prodrug inhibits liver colonies of rat sarcoma" Pharmacology/Therapeutics: Proc. of the American Assoc. for Cancer Res. (abstract) 38:10, 1997.

Schwartz et al., "Characterization of the Asialogylcoprotein Receptor in a Continuous Hepatoma Line" J. Biol. Chem. 256(17):8878-8881, 1981.

Schwartz et al., "Kinetics of Internalization and Recycling of the Asialoglycoprotein Receptor in a Hepatoma Cell Line" J. of Biol. Chem. 257(8):4230-4237, 1982.

Sharma et al., "Bioavailability study of oral and intravenous OGT 719, a novel nucleoside analogue with preferential activity in the liver" Cancer Chemother. Pharmacol. 48:197-201, 2001.

Plourde et al., "Targeted Therapy for Viral Hepatitis" Advanced Drug Delivery Reviews 17:311-315, 1995.

Fig. 3
Tri-antennary
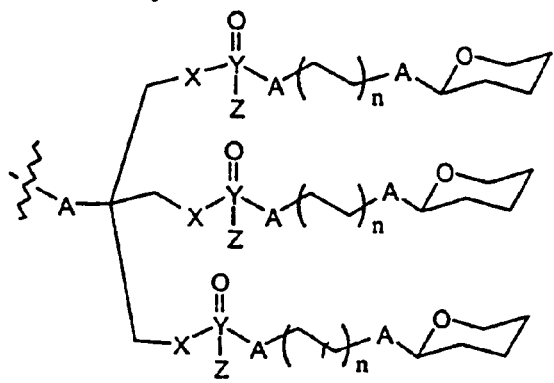
X = NH, O, S
Y = P or S
Z = NH-alkyl, NH$_2$, O$^-$, S$^-$
A = NH, CH$_2$, O, S
n = 2 to 17 2-carbon units
Carbohydrate =
tris((heteroatom)methyl)-[heteroatom]methane
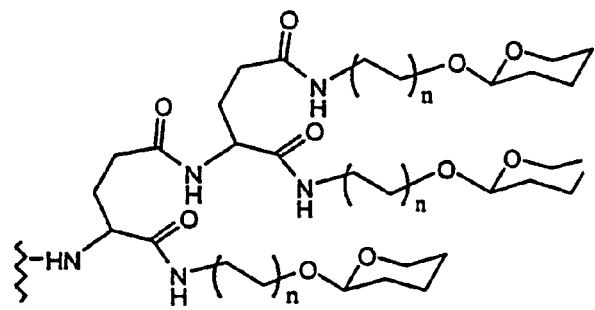
diglutamyl
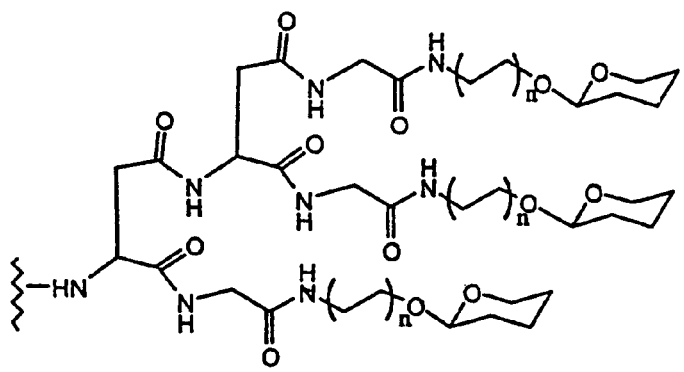
diasparatyl
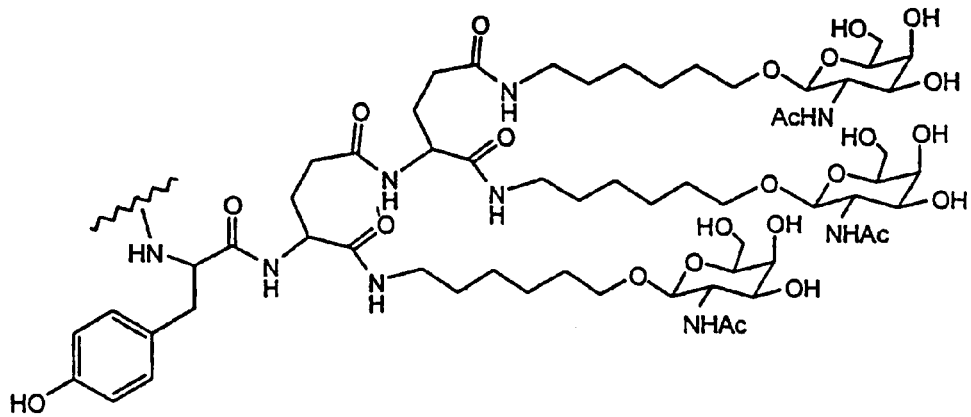

Fig, 3 (continued)
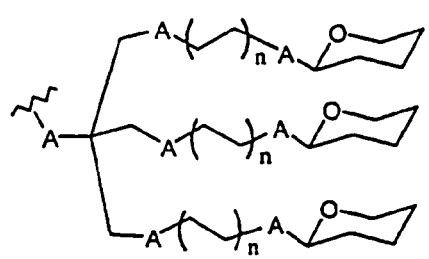
tris((heteroatom)methyl)-[heteroatom]methane
examples
tris(hydroxymethyl)aminomethane-based
[A= O]
tris(aminomethyl)aminomethane-based
[A= NH]
tris(thiomethyl)aminomethane-based
[A= S]
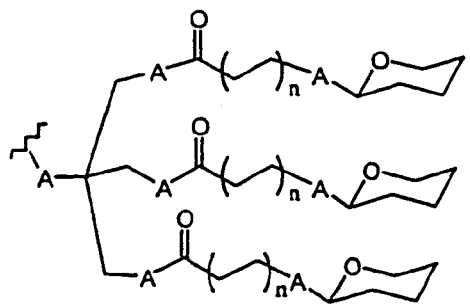
tris(aminomethyl)-[heteroatom]methane
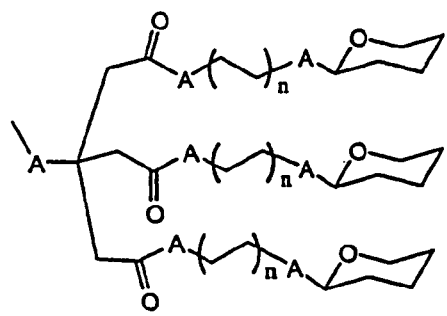
tris(acetoxy)-[heteroatom]methane
Tetra-antennary
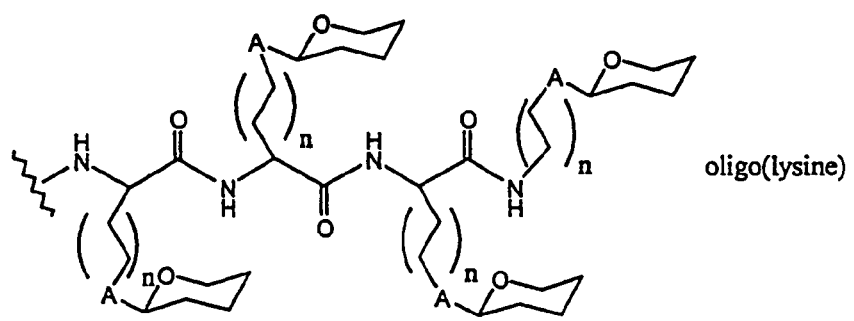
oligo(lysine)

Fig. 3 (Continued)
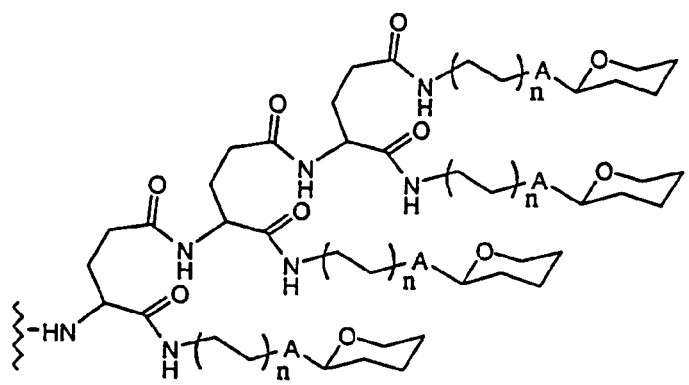
oligopeptide-based
(i.e. triglutamyl)
Multi-antennary
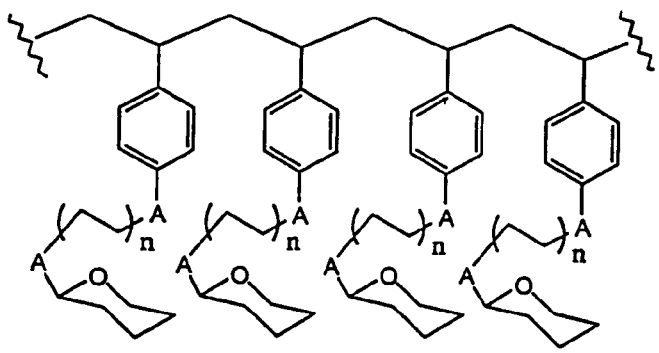
substituted
polystyrene-based
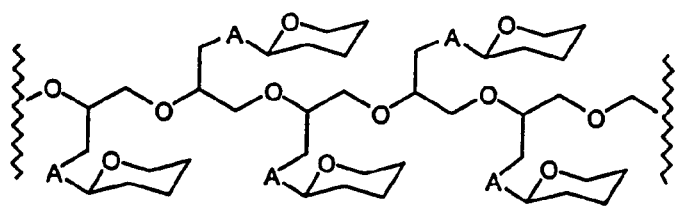
substituted
poly(ethyleneglycol)

Fig. 6
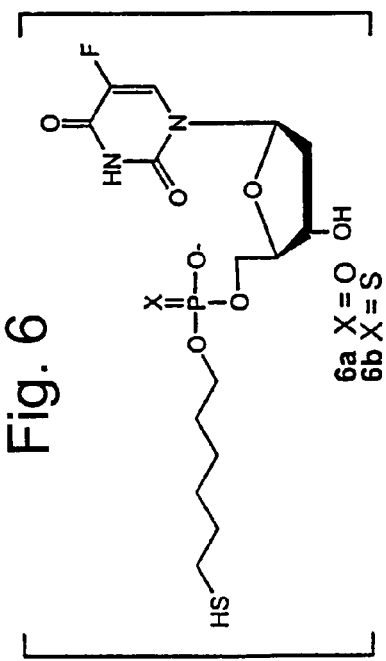
6a X = O
6b X = S
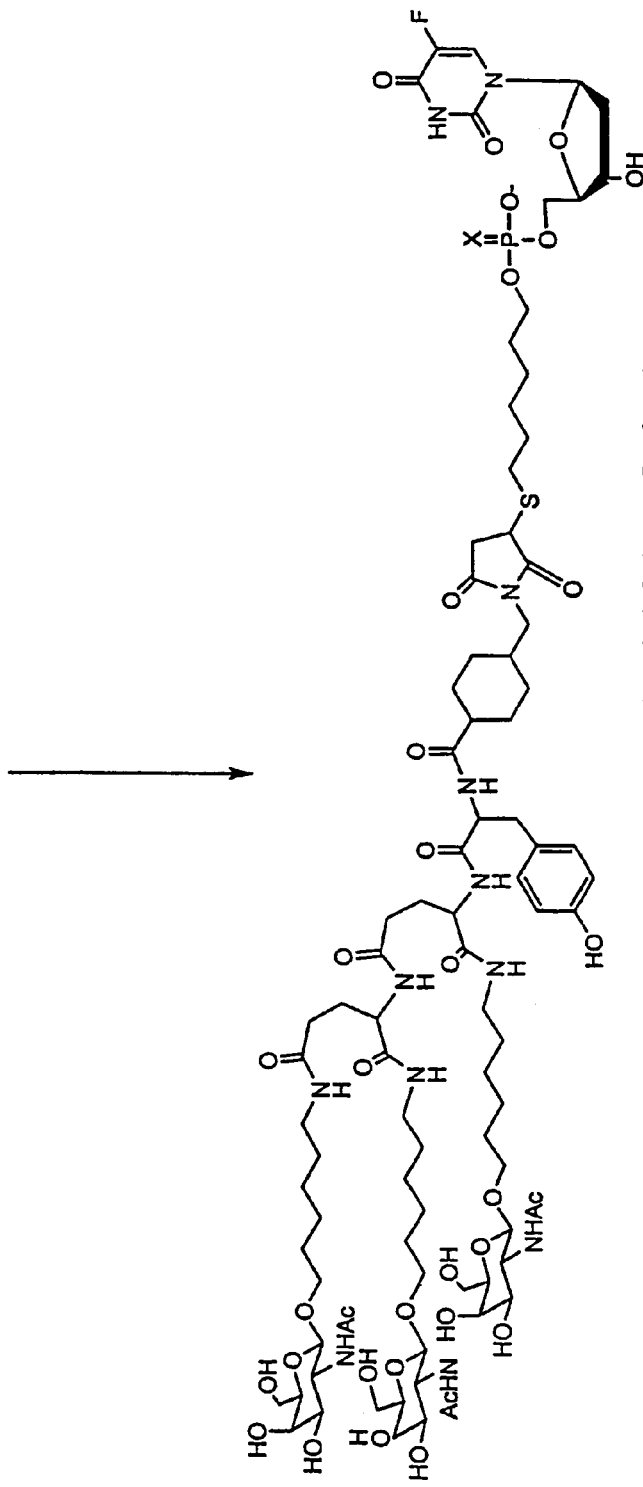
7a X = O; PO 1-mer Conjugate
7b X = S; PS 1-mer Conjugate Fig. 9
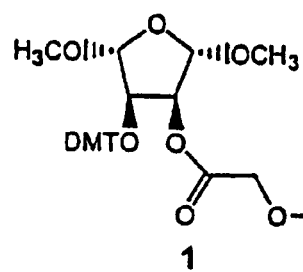
1
← Glass Bead
1) a. 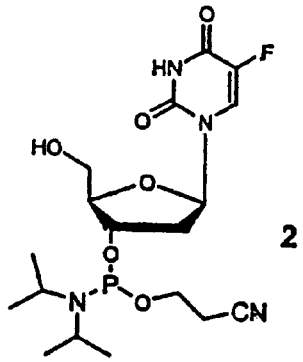
2
b. Cap A/Cap B
c. Beaucage Reagent
d. Cl₂CHCOOH
2) a. 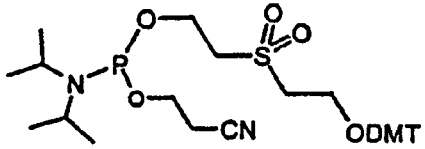
b. Cap A/Cap B
c. Beaucage Reagent
d. Cl₂CHCOOH
3) Cl₂CHCOOH
4) 0.5 M NaOH in 50% CH₃OH/H₂O, 1.5 h
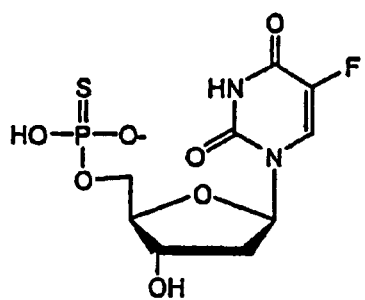
8

Fig. 11

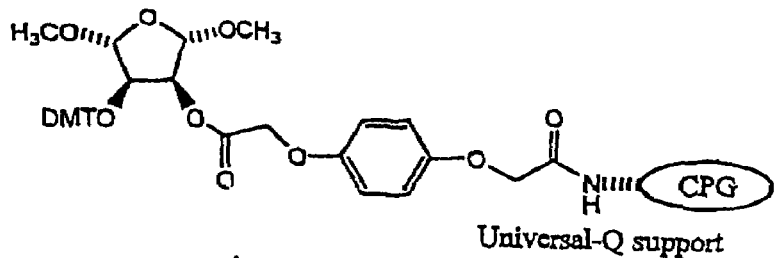
Universal-Q support

1) H+
2) 1H-tetrazole

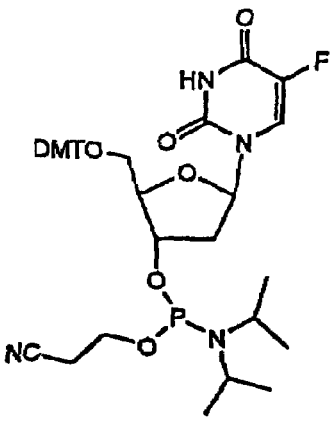

3) Oxidation - Beaucage Reagent
4) Capping - Acetic anhydride, 2,6-Lutidine Tetrahydrofuran
5) Repeat DMTO-FpsFpsFpsFpsFpsFpsFpsFpsFpsFpsFpsFpsFpsFpsFpsFpsF-Q 1) H+
2) 1H-tetrazole

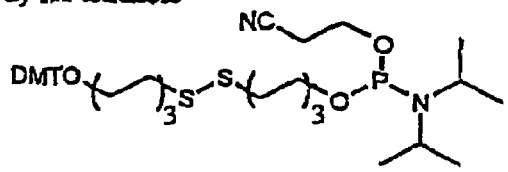

3) Oxidation - Beaucage Reagent
4) Capping - Acetic anhydride, 2,6-Lutidine Tetrahydrofuran
5) H+
6) 0.1 M NaOH in 50% $CH_3OH/H_2O$, 1h, 25°C
7) $C_{18}$ SepPak (Waters Corp.)

HO-$(CH_2)_6$-SS-$(CH_2)_6$-ps-FpsFpsFpsFpsFpsFpsFpsFpsFpsFpsFpsFpsFpsFpsFpsF

LINKER = SMCC-S-(CH2)6-
Ligand = YEE(ahGalNAc)3-
X = S or O.

n = 0-29 residues.

LINKER = SMCC-S-(CH₂)₆-
Ligand = YEE(ahGalNAc)₃-
X = S or O
n = 0-19 residues.

CONJUGATES OF GLYCOSYLATED/GALACTOSYLATED PEPTIDE, BIFUNCTIONAL LINKER, AND NUCLEOTIDIC MONOMERS/POLYMERS, AND RELATED COMPOSITIONS AND METHODS OF USE

CROSS-REFERENCE TO RELATED PATENT APPLICATIONS

This patent application is a continuation of U.S. application Ser. No. 09/998,497, filed Nov. 30, 2001, now U.S. Pat. No. 6,906,182 which claims the benefit of U.S. Provisional Patent Application No. 60/250,139, filed Dec. 1, 2000.

FIELD OF THE INVENTION

This invention relates to chemically defined, structurally homogeneous conjugates of glycosylated/galactosylated peptide, bifunctional linker, and nucleotidic monomers/polymers, compositions comprising same, and methods of use, such as in the inhibition of abnormal cellular proliferation and the inhibition of viral replication.

BACKGROUND OF THE INVENTION

Nucleotide and nucleic acid biosynthesis is fundamental to both the uncontrolled proliferation of cancer cells and the replication of viral pathogens. The ability of nucleoside analogues to interfere selectively with nucleotide and nucleic acid biosyntheses makes these compounds ideal anti-cancer and anti-viral agents. Nucleoside analogues inhibit the synthesis of nucleotides and nucleic acids by competing with their naturally occurring counterparts for the binding sites on enzymes that are involved in nucleic acid biosynthesis (Perigaud et al., *Nucleosides and Nucleotides*, 11:903 (1992)). Consequently, the formation of nucleic acid precursors, including nucleosides and nucleotides, is prevented. Furthermore, the incorporation of the analogues into nucleic acid molecules hinders the replication and/or transcription of these molecules. Therefore, the administration of nucleoside analogues to cancerous cells can inhibit their proliferation, whereas the administration of such analogues to virally infected cells can inhibit the replication of the infecting virus.

Because they are relatively small in size and electrostatically neutral, nucleoside analogues readily traverse the plasma membrane, facilitating passage to their intracellular target sites. However, the therapeutic effect of nucleoside analogues is severely limited by their dependence on intracellular enzymes for conversion into active inhibitors. The attachment of phosphate groups to the sugar residues of the nucleoside analogues is a necessary step for inhibiting nucleotide and nucleic acid biosynthesis. In some cases, nucleoside analogues must undergo two or more steps for conversion into active metabolites, thereby increasing the time it takes for them to act as inhibitors and the chance that the analogues will be converted to inactive metabolites, ultimately decreasing their effectiveness.

The dependence on intracellular enzymes for conversion into activating inhibitors is alleviated through the use of nucleotide analogues, which contain the phosphate groups. Although they offer a more direct mode of action in comparison to nucleoside analogues, the delivery of nucleotide analogues to the interior of a cell is severely hindered by the highly negative charge of the phosphate group. Therefore, a mechanism by which nucleotide analogues are delivered to their intracellular targets is desired.

Gmeiner et al. (U.S. Pat. No. 5,457,187) discloses the delivery of the nucleotide analogue, 5-fluorodeoxyuridine 5' monophosphate, through covalent attachment of lipophilic or cationic moieties, including cholesterol, ethyl-spaced adamantane, 1,2-dihexadecylglycerol and poly-L-lysine. The entry into cells is further enhanced by delivering the analogue as a homo-oligomer. Although these conjugates provide a mechanism of drug delivery to the interior of the cell, they do not target the nucleotide analogue to specific tissues or cells.

As with most drugs, the clinical application of nucleotide analogues is limited by their failure to reach the targeted cell population and by the toxicity they impose on non-targeted cells. Tissue-specific drug targeting would not only reduce systemic toxicity but would also potentiate drug action by concentrating the drug in target cells or tissues (Wadhwa et al., *J. Drug Targeting* 3:111 (1995)). Targeting nucleotide analogues in a tissue-specific manner is, therefore, desired.

Several tissue-specific drug targeting strategies have consequently come about in an attempt to overcome these problems. One such strategy, carrier-mediated drug targeting, involves either the covalent or non-covalent association of a drug with a tissue-specific targeting moiety. In a subclass of this strategy, termed active targeting, the targeting moiety is a ligand that is recognized by a specific receptor, which is found predominantly at the target site. Ligand binding to the receptor results in receptor-mediated endocytosis, wherein the drug-ligand conjugate is internalized, along with the receptor, by the target cell. Once inside the cell, the conjugate is susceptible to intracellular enzymes that cleave the bond between the ligand and drug, resulting in the release of the drug from the conjugate. In this manner, the delivery of therapeutic agents to targeted cell populations is achieved.

Ligand-directed, receptor-mediated endocytosis is the basis upon which several drug targeting systems rely. Antibodies, or fragments thereof, hormones, cytokines, and other soluble proteins, such as gastrin and transferrin, have all been employed as targeting ligands for the delivery of drugs to specific cell populations. For example, Myers et al. (U.S. Pat. No. 5,087,616) discloses a drug delivery conjugate wherein the drug, daunomycin, is delivered to epithelial cells specifically via conjugation to the hormone ligand epithelial growth factor. Also, Gmeiner et al. (U.S. Pat. No. 5,663,321) discloses the delivery of a homo-oligomer comprising monomers of the nucleotide analogue, 5-fluorodeoxyuridine 5' monophosphate, through attachment to an antibody or fragment thereof.

Ligands are not always protein in nature, however. Carbohydrate moieties serve as the ligands for a family of receptors known as lectins. These receptors vary, based on their tissue expression and ligand specificity. For instance, the lectin found on Kupffer cells is specific for mannose, whereas the lectin found on hepatic endothelial cells binds selectively to fucose residues.

The asialoglycoprotein receptor (ASGPR), a lectin found predominantly on the surface of hepatocytes, has been studied in depth for the purpose of delivering therapeutic agents to the liver. Because it mediates high affinity interactions with practically any entity that contains terminal galactose or acetylgalactosamine residues, irrespective of the size or structure of the entity, the ASGPR is a model system to use for drug delivery. Pioneering work by Wu et al. (*J. Biol. Chem.* 262:4429 (1987)) demonstrated that antisense oligonucleotides electrostatically complexed to poly-L-lysine that is linked to asialoorosomucoid, a galactose/acetylgalactosamine-containing protein, are efficiently and specifically taken into human hepatocellular carcinoma cells through direct interaction with the ASGPR. However, because the antisense oligonucleotides were non-covalently attached to the targeting moiety, it is reasonable to assume that the resulting conjugate was less biostable than if it were covalently bonded.

Tissue-specific drug targeting through use of the ASGPR has been applied to the delivery of nucleotide analogues. For instance, Groman et al. (U.S. Pat. No. 5,554,386) discloses a conjugate comprising the nucleotide analogue, araAMP, and the polysaccharide, arabinogalactan, which binds to the ASGPR, for delivery of the drug to hepatocytes. Because polysaccharides contain multiple drug attachment sites, however, the synthesis of this conjugate would result in a heterogeneous mixture of conjugates, wherein the number of nucleotide analogues per conjugate varies from batch to batch. Consequently, the $IC_{50}$ of the conjugate would also vary from batch to batch, making it very difficult to determine the dose for administration.

Rohlff et al. (*Cancer Research* 59:1268 (1999)) discloses a drug-ligand conjugate, OGT719, wherein a single galactose moiety is covalently attached to the nucleoside analogue, 5-fluorouracil. Although shown to be effective in animal models, this drug conjugate is predicted to bind weakly to the ASGPR in view of the studies conducted by Lee et al. (*Biochemistry* 23: 4255 (1984)), in which ligands containing three or four galactose residues arranged in a specific conformation bind with much greater affinity to the ASGPR than a single residue. High affinity binding conjugates are desired so that lower doses of the conjugates can be administered for achievement of the desired therapeutic effects.

Taken together, a conjugate capable of undergoing ligand-directed, receptor-mediated endocytosis for the delivery of nucleotide analogues to their intracellular targets in a tissue-specific manner is desired. The components that comprise the conjugate should be covalently bonded to each other for maximum biostability. The conjugate should be chemically defined and structurally homogeneous such that a single $IC_{50}$ can be determined. The conjugate also should bind with high affinity to a targeted receptor. A conjugate with these properties would have an improved therapeutic index. It is an object of the present invention to provide such a conjugate. This and other objects and advantages, as well as additional inventive features, will become apparent from the detailed description provided herein.

SUMMARY OF THE INVENTION

The present invention provides a chemically defined, structurally homogeneous conjugate of formula A-L-P, in which:

A represents a glycosylated/galactosylated peptide that binds to a cell-surface receptor on a cell, L represents a bifunctional linker, which does not comprise a naturally occurring amino acid and which is covalently bonded to A and P in a regiospecific manner, and P represents a monomer, homopolymer or heteropolymer comprising at least one nucleotide or an analogue thereof, which inhibits the intracellular biosynthesis of nucleotides or nucleic acids in a sequence-independent manner, wherein either or both of the covalent bond between A and L and the covalent bond between L and P can be cleaved intracellularly. When A is glycosylated, the cell-surface receptor is on a cell of which the liver is comprised. When A is galactosylated, the cell-surface receptor is an asialoglycoprotein receptor. Also provided is a composition comprising such a conjugate.

The present invention further provides a method of inhibiting abnormal cellular proliferation in a mammal in need thereof. The method comprises administering to the mammal an abnormal cellular proliferation-inhibiting amount of an above-described conjugate or a composition comprising same, whereupon the abnormal cellular proliferation in the mammal is inhibited.

Still further provided by the present invention is a method of inhibiting replication of a virus in a mammal. The method comprises administering to the mammal a viral replication-inhibiting amount of an above-described conjugate or a composition comprising same, whereupon the replication of the virus in the mammal is inhibited.

BRIEF DESCRIPTION OF THE FIGURES

FIG. 3 depicts examples of tri-, tetra-, and multi-antennary ligands.

FIG. 6 depicts synthesis of YEE(ahGalNAc)$_3$-SMCC-5-fluoro-2'-deoxyuridine conjugates, po-1-mer and ps-1-mer.

FIG. 9 depicts removal from solid support and synthesis of 5'-thiophosphate 5-fluoro-2'-deoxyuridine.

FIG. 11 depicts synthesis of 5-fluoro-2'-deoxyuridine-containing oligonucleotides (18-mer).

DETAILED DESCRIPTION OF THE INVENTION

Figure 1:
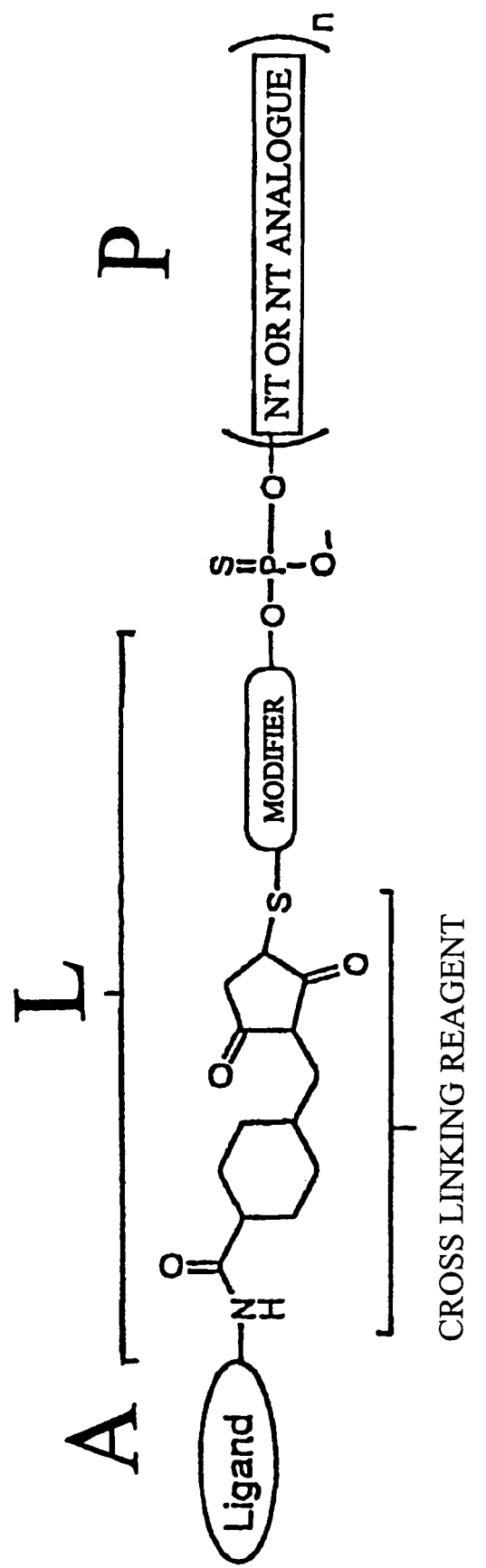
FIG. 1 depicts a schematic of the "A-L-P" conjugate, wherein A comprises a ligand, L comprises a cross-linking reagent and a modifier, and P comprises n nucleotides or analogues thereof, wherein n=number of nucleotides or analogues thereof.

The present invention provides a chemically defined, structurally homogeneous conjugate of formula A-L-P, in which:

A represents a glycosylated peptide that binds to a cell-surface receptor on a cell of which the liver is comprised, L represents a bifunctional linker, which does not comprise a naturally occurring amino acid and which is covalently bonded to A and P in a regiospecific manner, and P represents a monomer, homopolymer or heteropolymer comprising at least one nucleotide or an analogue thereof, wherein said nucleotide or analogue thereof inhibits the intracellular biosynthesis of nucleotides or nucleic acids in a sequence-independent manner, wherein either or both of the covalent bond between A and L and the covalent bond between L and P can be cleaved intracellularly.

The invention also provides a chemically defined, structurally homogeneous conjugate of formula A-L-P, in which:

A represents a galactosylated peptide that binds to a cell-surface asialoglycoprotein receptor on a cell, L represents a bifunctional linker, which does not comprise a naturally occurring amino acid and which is covalently bonded to A and P in a regiospecific manner, and P represents a monomer, homopolymer or heteropolymer comprising at least one nucleotide or an analogue thereof, wherein said nucleotide or analogue thereof inhibits the intracellular biosynthesis of nucleotides or nucleic acids in a sequence-independent manner, wherein either or both of the covalent bond between A and L and the covalent bond between L and P can be cleaved intracellularly.

The term "chemically defined," as used herein, describes an entity that has an exact chemical formula, for instance, $C_6H_{12}O_2$. The molecular weight of a chemically defined entity is absolute, such that it is not an average molecular weight. Furthermore, the molecular weight does not vary upon batch synthesis.

The term "chemically uniform," as used herein, means that at least 95% of the delivery assembly, and most preferably at least 99%, is a single species in composition and connectivity. Chemical uniformity can be determined by polyacrylamide gel electrophoresis, reverse-phase high-pressure liquid chromatography, nuclear magnetic resonance, mass spectrometry and chemical analysis. The phrase "chemically defined, structurally homogeneous" is used interchangeably with "chemically uniform."

The term "structurally homogeneous" as used herein describes an entity that is characterized by an absolute ratio of components. For example, the present invention is a conjugate comprising components A, L and P, wherein only one A, one L and one P exist per conjugate. The 1:1:1 ratio of A:L:P components does not vary upon batch synthesis.

A "nucleoside" is a compound comprising a base and a sugar. A "nucleotide" is a compound composed of a base, a sugar, as defined above, and a phosphate group, which is also referred to as a mononucleotide. The bases of nucleotides and nucleosides can be, but are not limited, to purines and pyrimidines. The sugars of nucleotides and nucleosides can be, but are not limited to, ribose and deoxyribose. Purines include, for example, adenine and guanine. Pyrimidines include, for instance, cytosine, uracil and thymine.

A "nucleoside analogue" is a naturally occurring nucleoside that contains at least one modification at the sugar or base moiety. Modifications of nucleoside analogues include, for example, substitution of one or several sugar atoms, heterocyclic base modifications, nucleosidic linkage displacement on the sugar, anomeric inversion ($\beta \rightarrow \alpha$), addition of various functional groups on the cyclic carbons of the sugar residues, substitution or elimination of hydroxyl groups of the sugar residues, modifications of the ring size, inversion of the configuration of the sugar ($D \rightarrow L$), and furanose ring breaking into acyclonucleosides.

It is understood by one of ordinary skill in the art that any nucleoside analogue can be phosphorylated, such that it is a nucleotide analogue. The term "nucleotide analogue" is a moiety that has at least one non-naturally-occurring portion, and which functions similarly to or superior to a naturally occurring nucleotide. Nucleotide analogues can have, for example, altered sugar moieties, bases or inter-sugar linkages. Modifications of nucleotide analogues include those that are described above for nucleoside analogues, in addition to alterations in the atoms or functional groups bonded to the phosphorus atom of the phosphate groups. These include, but are not limited to, alterations that can result in "non-phophodiester internucleotide bonds," i.e., a linkage other than a phosphodiester (see, e.g., Waldner, et al., *Bioorganic and Medicinal Chemistry Letters*, 6(19), 2363-2366 (1996)). Methylphosphonate internucleotide linkages, phosphothioate internucleotide linkages, and combinations thereof are examples of "non-phosphodiester internucleotide bonds." Some, one, none or all internucleotide linkages of the polymers comprising nucleotides or nucleotide analogues can be replaced with these modified linkages.

The moiety "P" includes any suitable nucleotide or analogue thereof that inhibits the intracellular biosynthesis of nucleotides or nucleic acids in a sequence-independent manner. It is understood by one of ordinary skill in the art that inhibition does not require complete inhibition, as a beneficial or therapeutic effect can be realized with any degree of inhibition. Rather, there are varying degrees of inhibition. The term "sequence-independent manner," as used herein, shall refer to the unimportance of the base sequence of the nucleotides or analogues thereof of which P is comprised. "P" is not an antisense oligonucleotide, as that term is used in the art, i.e., in the inhibition of transcription or translation. Whether or not a given nucleotide or analogue thereof inhibits the intracellular biosynthesis of nucleotides and nucleic acids can be determined in accordance with assays known in the art and exemplified herein.

Suitable nucleotide analogues can comprise any number of nucleoside analogues. Nucleoside analogues include, but are not limited to, aglycone-modified nucleoside analogues, which can comprise, for example, a fluorinated pyrimidine. The fluorinated pyrimidine can be, for instance, 5-fluorouracil (5FU). The aglycone-modified nucleoside analogue alternatively can be 5-fluoro-2'-deoxyuridine (5FdU), or it can be an azapyrimidine nucleoside, such as 5-azacytidine (also known as 5-azaCyd or 4-amino-1-($\beta$-D-ribofuranosyl-1,3,5,-triazin-2-one)), 5-azauridine (5-AzaUrd), 6-azacytidine (6-AzaCyd), or 6-azauridine (6-AzaUrd). Moreover, the aglycone-modified nucleoside analogue can be a 3-deazapyrimidine nucleoside, such as 3-deazauridine (3-DeazaUrd). Nucleoside analogues also include sugar-modified nucleosides, such as AraC (also known as 1-$\beta$-D-arabinofuranosylcytosine, cytosine arabinoside, cytarabine, and cytosar), cyclocytidine, 2'-O-nitro-AraC, AraA, (also known as 9-$\beta$-D-arabinofuranosyladenine, vidarabine, and vira-A), cyclaridine, 2', 2'-difluorodeoxycytidine (gemcitabine), and 2'-deoxy-2'-methylidene-cytidine (DMDC). The sugar-modified nucleoside can be an acyclonucleoside, such as acyclovir (also referred to as 9-(2-hydroxyethoxymethyl) guanine, acycloguanosine, and ACV) or gancyclovir (also known as cytovene, DHPG, 9-(1,3-dihydroxy-2-propoxymethyl)guanine, 2'-Nor-2'-deoxyguanosine, 2'NDG, BIOLF-62, or BW B759U).

Nucleoside analogues additionally include fludarabine phosphate, 2-haloadenine-2'-deoxyribonucleoside, 2-chloroadenine-arabinonucleoside, 2'-deoxycoformycin, and 2-halo-2'-fluoroarabinonucleoside. One in the art will recognize that other nucleoside analogues, not mentioned specifically herein by name, can be used in the context of the present invention and are readily available commercially.

"P" is a monomer, homopolymer, or heteropolymer comprising at least one oligonucleotide or analogue thereof. "P" is a monomer when it comprises one nucleotide or analogue thereof. "P" is a homopolymer when it comprises at least two nucleotides or analogues thereof, wherein the at least two nucleotides are the same. When "P" comprises at least two nucleotides or analogues thereof and at least one nucleotide or analogue thereof is different from the other nucleotides or analogues thereof, "P" is a heteropolymer. For example, "P" can be a monomer, homopolymer, or heteropolymer comprising 5FdU. When "P" is a homo- or heteropolymer, the number of units can be 2 to 50, 2 to 40, 2 to 30, 2 to 20, preferably 2 to 12, more preferably 2 to 6, and most preferably 2 to 4. In a preferred embodiment, "P" is a homopolymer of 5FdU. Preferably, "P" is a homopolymer containing 2 to 12 5FdU and, more preferably, "P" is a homopolymer containing 2 to 6 5FdU. An especially preferred "P" is a monomer of 5FdU.

When "P" is a hetero- or homopolymer, each of the nucleotides or analogues thereof is covalently bonded to the adjacent nucleotides or analogues thereof. Desirably, at least one of the covalent bonds can be cleaved intracellularly. Preferably, all of the internucleotidic covalent bonds can be cleaved intracellularly. Any suitable internucleotidic covalent bond can be employed. Preferred covalent bonds include a phosphodiester bond (po) or a phosphothioate bond (ps). Internucleotidic covalent bonds in a homopolymer or heteropolymer can be the same or different, and can alternate, for example. Preferably, the internucleotidic covalent bonds in a homopolymer or heteropolymer are the same. In order to monitor the delivery and/or efficacy of ALP, "P" can comprise a radioactive nuclide.

"A" is a glycosylated peptide that binds to a cell-surface receptor on a cell of which the liver is comprised or a galactosylated peptide that binds to a cell-surface asialoglycoprotein receptor on a cell, nonlimiting examples of which are provided in FIG. 3. A "glycosylated peptide" as used herein is any polyamide that contains at least one carbohydrate (i.e., mono- or polysaccharide) moiety. Preferably, "A" is a glycosylated oligopeptide. A "galactosylated peptide" as used herein is any polyamide that contains at least one galactose residue. Preferably, "A" is a galactosylated oligopeptide. "A" is a synthetic, chemically defined, structurally homogeneous oligopeptide scaffold that is glycosylated with any of a number of sugar residues including, but not restricted to, glucose, N-acetylglucosamine, galactose, N-acetylgalactosamine, mannose, and fucose. Preferably, "A" is

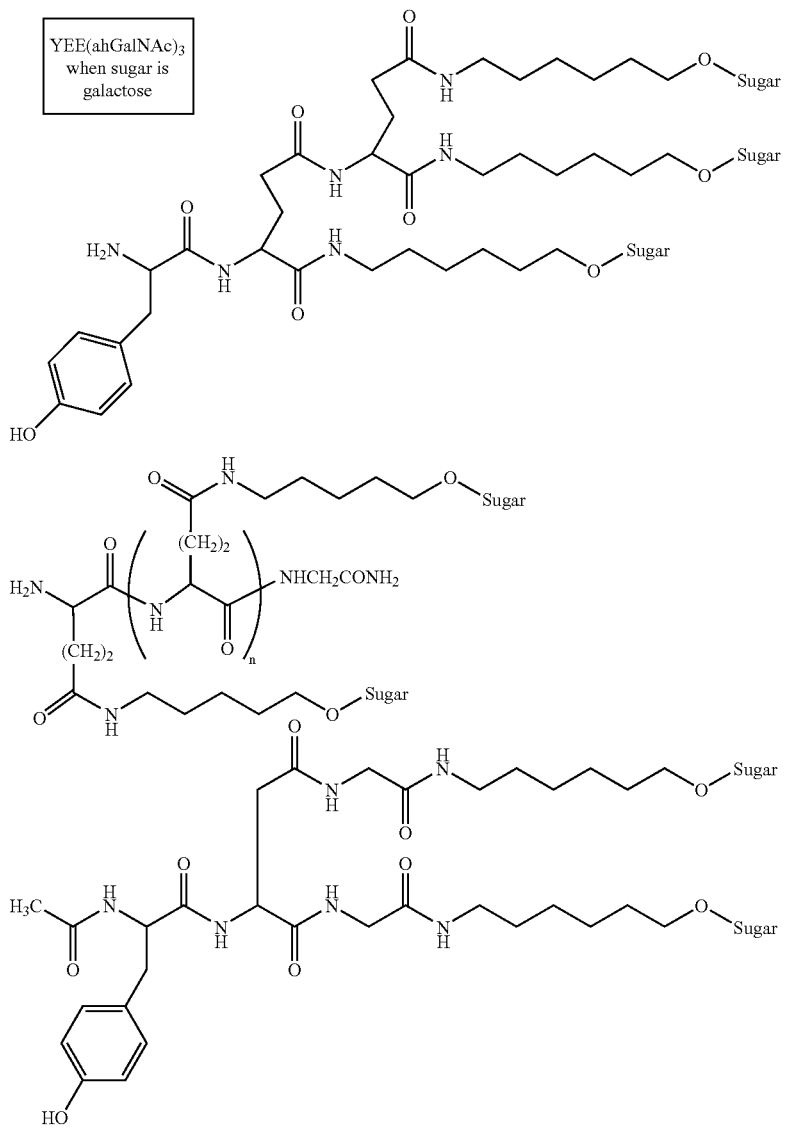

-continued

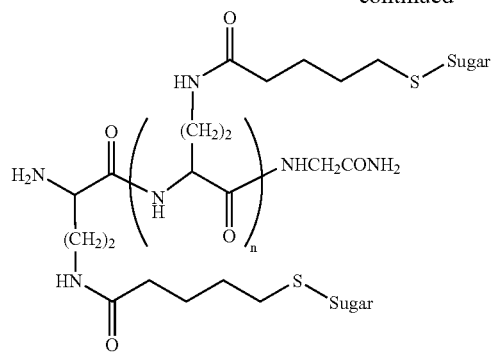

of which YEE(ahGalNAc)₃ is especially preferred. Suitable "A" compounds can be prepared using methods known in the art (see, e.g., Lee et al., *Biochem*, 23: 4255-4261 (1984); Lee et al., *J. Carbohydrate Chemistry*, 5(3): 343-357 (1986); Lee et al., *Targeted Diagn. Ther.*, 4: 65-86 (1991); Lee, *Carbohydrate Research*, 67: 509-514 (1978)).

"L" is a bifunctional linker, which does not comprise a naturally occurring amino acid or a peptide formed from naturally occurring amino acids. "L" is covalently bonded to "A" and "P" in a regiospecific manner. Any suitable linker can be used. Desirably "L" is heterobifunctional.

Suitable linkers are products of cross-linking reagents that are commercially available (e.g., Pierce Chemical Co.). Typically, the cross-linking reagents contain reactive groups only at the ends that are capable of linking to "A" and "P" in a regiospecific manner, thereby reducing the potential for unwanted side reactions. A wide variety of cross-linking reagents are available that are capable of reacting with various functional groups present on "A" and "P." Thus, many chemically distinct linkages can be conjugated. Preferably, L is a product of a cross-linking reagent that comprises an active ester, isothiocyano, isocyano, acyl, halo, maleimido, or active disulfido group. For example, "L" can be a product of the cross-linking reagent:

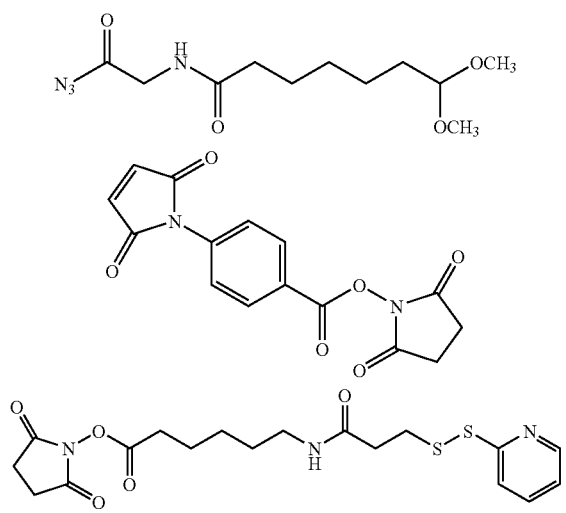

-continued

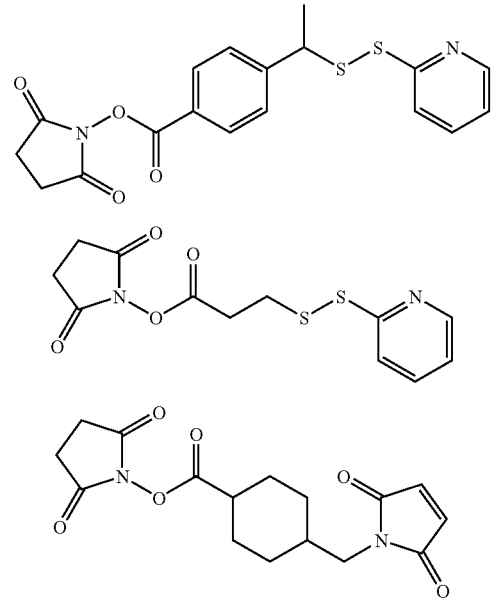

or α-citraconyl-K-(ε-FMOC)PILFFRL (N-a-citraconyl-Lys (eFMOC)-Pro-Ile-Leu-Phe-Phe-Arg-Lys-COOH). Preferably, L is a product of the cross-linking reatent N-hydroxysuccinimidyl 4-(N-methylmaleimido) cyclohexyl-1-carboxylate (SMCC).

In a specific example of "A," YEE(ahGalNAc)₃ (FIG. 3) contains a free amino group at its amino terminus. It will react regiospecifically and site specifically with the heterobifunctional cross-linking reagent SMCC to form an amide bond. The nucleotide or analogue thereof, if chemically modified to contain a free sulfhydryl group, will chemically combine with SMCC to form a thioether linkage. In this example, the linkage formed between "A" and "P" could be summarized as amide/thioether. Preferably, "A" is covalently bonded to "L" through an amide bond and "L" is covalently bonded to "P" through a thioether bond. Other linkages between "A" and "P" via "L" include, but are not restricted to, amide/amide, thioether/amide, disulfide/amide, amide/thioether, and amide/disulfide. The linkages can be further categorized as biologically stable (thioether, amine), somewhat biologically stable (amide), and biologically labile (disulfide). Thus, the delivery system can be modified structurally to function in the various chemical environments encountered in the extra-and intracellular medium.

A preferred conjugate of the present invention is one in which "A" is YEE(ahGalNAc)$_3$, "L" is the product of cross-linking reagent SMCC, and "P" comprises at least one 5FdU. While "P" can be a homopolymer of 5FdU, preferably "P" is a monomer of 5FdU.

The present invention further provides a composition comprising an above-described conjugate. Preferably, the composition further comprises a pharmaceutically acceptable carrier. Suitable "pharmaceutically acceptable carriers" are known in the art. Typically, the pharmaceutical composition can comprise a physiological saline solution; dextrose or other saccharide solution; or ethylene, propylene, polyethylene, or other glycol.

One skilled in the art will appreciate that suitable methods of administering a A-L-P conjugate or composition thereof to an animal, e.g., a mammal such as a human, are known, and, although more than one route can be used to administer a particular composition, a particular route can provide a more immediate and more effective reaction than another route. The choice of carrier will be determined, in part, both by the particular composition and by the particular method used to administer the composition. Accordingly, there is a wide variety of suitable formulations of the compositions of the present invention.

Formulations suitable for oral administration can consist of (a) liquid solutions, such as an effective amount of the conjugate dissolved in diluents, such as water or saline, (b) capsules, sachets or tablets, each containing a predetermined amount of the active ingredient, as solids or granules, (c) suspensions in an appropriate liquid, and (d) suitable emulsions.

Tablet forms can include one or more of lactose, mannitol, cornstarch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

Formulations suitable for parenteral administration include aqueous and non-aqueous solutions, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The conjugates of the present invention can be administered alone or in combination with other suitable components. Such components include those that help the therapeutic agent (i.e., "P") inhibit abnormal cellular proliferation or viral replication more effectively. For example, the ligand-derived leucovorin (folinic acid) can be co-administered in order to enhance the effectiveness of 5FdU.

In view of the above, the present invention also provides a method of inhibiting abnormal cellular proliferation in a mammal in need thereof. The method comprises administering to the mammal an abnormal cellular proliferation-inhibiting amount of an above-described conjugate or composition, whereupon the abnormal cellular proliferation in the mammal is inhibited. An "abnormal cellular proliferation-inhibiting amount" of a conjugate is that amount of conjugate sufficient to inhibit to any degree the abnormal cellular proliferation. Preferably, the abnormal cellular proliferation is hepatocellular carcinoma. The present inventive conjugates and compositions are also therapeutically useful in treating other diseases and disorders of the liver, such as neoplastic and infectious diseases and disorders.

Also in view of the above, the present invention provides a method of inhibiting replication of a virus in a mammal in need thereof. The method comprises administering to the mammal a viral replication-inhibiting amount of an above-described conjugate or composition, whereupon the replication of the virus in the mammal is inhibited. A "viral replication-inhibiting amount" of a conjugate is that amount of a conjugate sufficient to inhibit to any degree the viral replication. Preferably, the viral replication is hepatitis viral replication.

The dose administered to an animal, particularly a human, in the context of the present invention should be sufficient to effect a therapeutic response in the animal over a reasonable time frame. The dose will be determined by the strength of the particular compositions and the condition of the animal (e.g., human), as well as the body weight of the animal (e.g., human) to be treated. The size of the dose also will be determined by the existence, nature, and extent of any adverse side effects that might accompany the administration of a particular composition. A suitable dosage for internal administration is 0.01 to 100 mg/kg per day. A preferred dosage is 0.01 to 35 mg/kg per day. A more preferred dosage is 0.05 to 5 mg/kg per day. A suitable concentration of the conjugate in pharmaceutical compositions for topical administration is 0.05 to 15% (by weight). A preferred concentration is from 0.02 to 5%. A more preferred concentration is from 0.1 to 3%. Ultimately, the attending physician will decide the dosage and the amount of conjugate of the present invention with which to treat each individual patient, taking into consideration a variety of factors, such as age, body weight, general health, diet, sex, composition to be administered, route of administration, and severity of the disease being treated.

EXAMPLES

The following examples serve to illustrate the present invention and are not intended to limit its scope in any way.

Abbreviations

For convenience, the following abbreviations are used: AET, 2-aminomercaptoethanol (aminoethanethiol); ATP, adenosine triphosphate; BAP, bacterial alkaline phosphatase; CPG, controlled pore glass support; DIPEA, diisopropylethylamine; D-MEM, Dulbecco's modified Eagle's medium; DMSO, dimethyl sulfoxide; DPBS, Dulbecco's phosphate buffered saline; DTT, dithiothreitol; EDAC, 1-ethyl-3-[3(dimethylamino)propyl] carbodiimide; EDTA, ethylenediaminetetraacetate; FCS, fetal calf serum; GalNAc, N-acetylgalactosamine; MEM, minimal essential medium with Earle's salts; SMCC, N-hydroxysuccinimidyl 4-(N-methylmaleimido)cyclohexyl-1-carboxylate; Tris, tris (hydroxymethyl)amine; PNK, phenylnucleotidekinase; Hep G2, human hepatomacellular carcinoma; TSV, human prostate adenocarcinoma; Caki-1, human kidney cells; HBSS, Hank's balanced saline solution salt; RPMI, Roswell Park Memorial Institute; po 1-mer, phosphodiester mononucleotide conjugate; ps 1-mer, phosphothioate mononucleotide conjugate; 5FU 1-mer, 5-fluorouracil mononucleotide conjugate; AFP, alpha-fetoprotein.

Example 1

Figure 4:
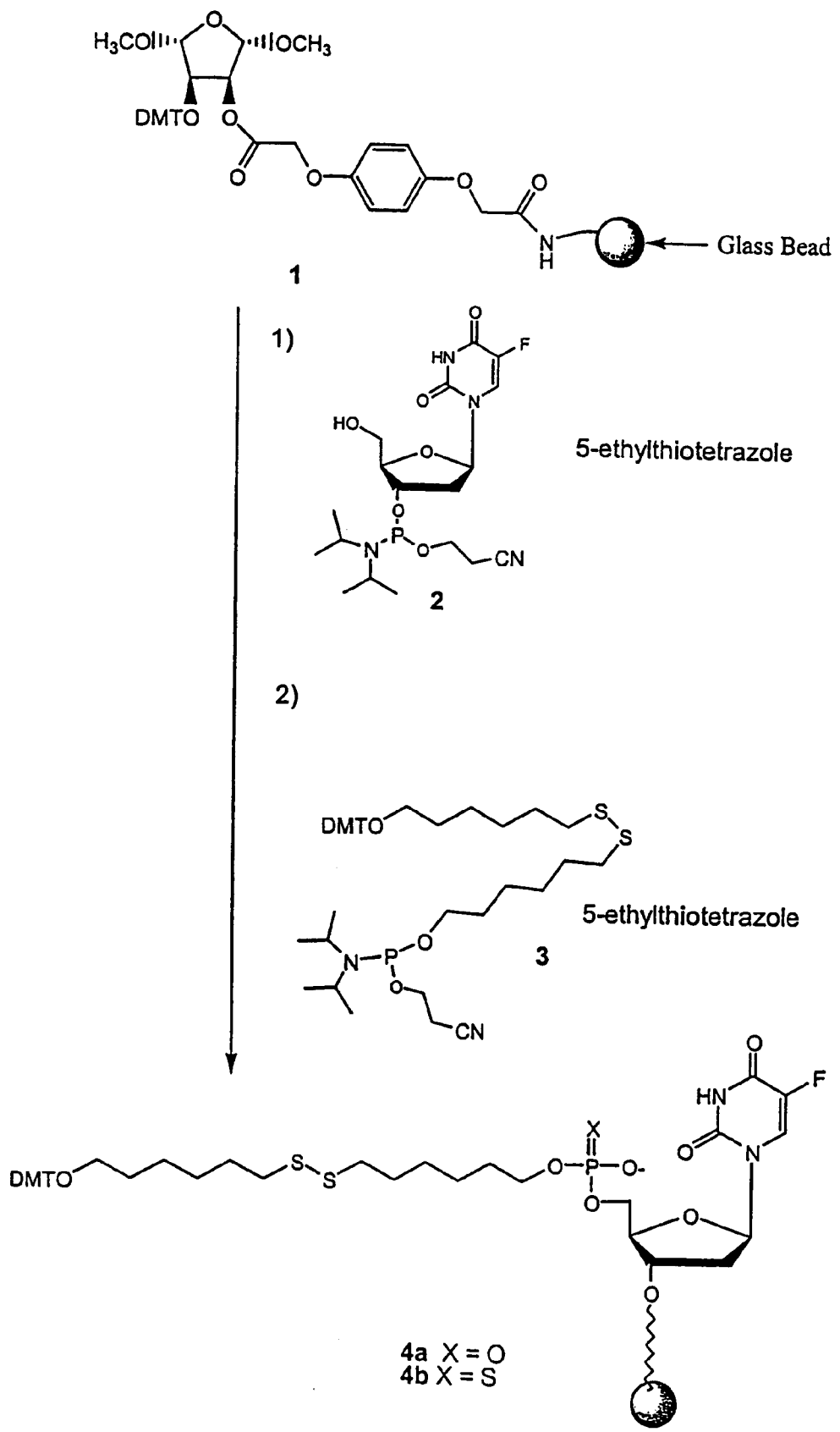
FIG. 4 depicts automated synthesis of 5'-C6-disulfide 5-fluoro-2'deoxyuridine.

This example describes the synthesis of the 5'-C6 disulfide 5-fluoro-2'-deoxyuridine mononucleotide (4a and 4b, FIG. 4)

A 15-μmole column was prepared using 0.3701 g (26 μmole/g loading capacity) of the Universal-Q CPG (1, FIG. 4) and placed on one of the two reaction ports of a Millipore Expedite DNA/RNA synthesizer. Specifically, a $CH_3CN$ solution containing the 5-fluoro-2'-deoxyuridine synthon (0.25 g in 5 ml of $CH_3CN$) was placed in the "T" bottle, and the C6 disulfide phosphoramidite synthon (3, FIG. 4) was placed in the "5" bottle (see, e.g., Smith et al., *Nucleosides and Nucleotides*, 15(10), 1581-1594 (1996)). The automated synthesis was carried out sequentially (from the 3'→5'-end), and entailed the reaction of the 5-fluoro-2'-deoxyuridine phosphoramidite synthon (2, FIG. 4) with the solid support followed by treatment with the thiol modifier synthon (3, FIG. 4). For the phosphodiester-linked compound, the standard oxidizing solution (3% $I_2$ in a solution of tetrahydrofuran/pyridine/$H_2O$); Glen Research Inc., Sterling, Va.) was used. When necessary, Beaucage reagent (Glen Research Inc.) was substituted for the oxidizer solution to effect sulfurization of the phosphite to give the phosphorothioate according to standard established procedures. This reagent was used at a concentration 100 mg reagent in 10 ml of anhydrous $CH_3CN$. Standard oxidation times were followed (30 sec for both phosphodiester- and phosphorothioate-linked compounds). The final 5'-DMT was left on in order to facilitate purification.

Figure 5:
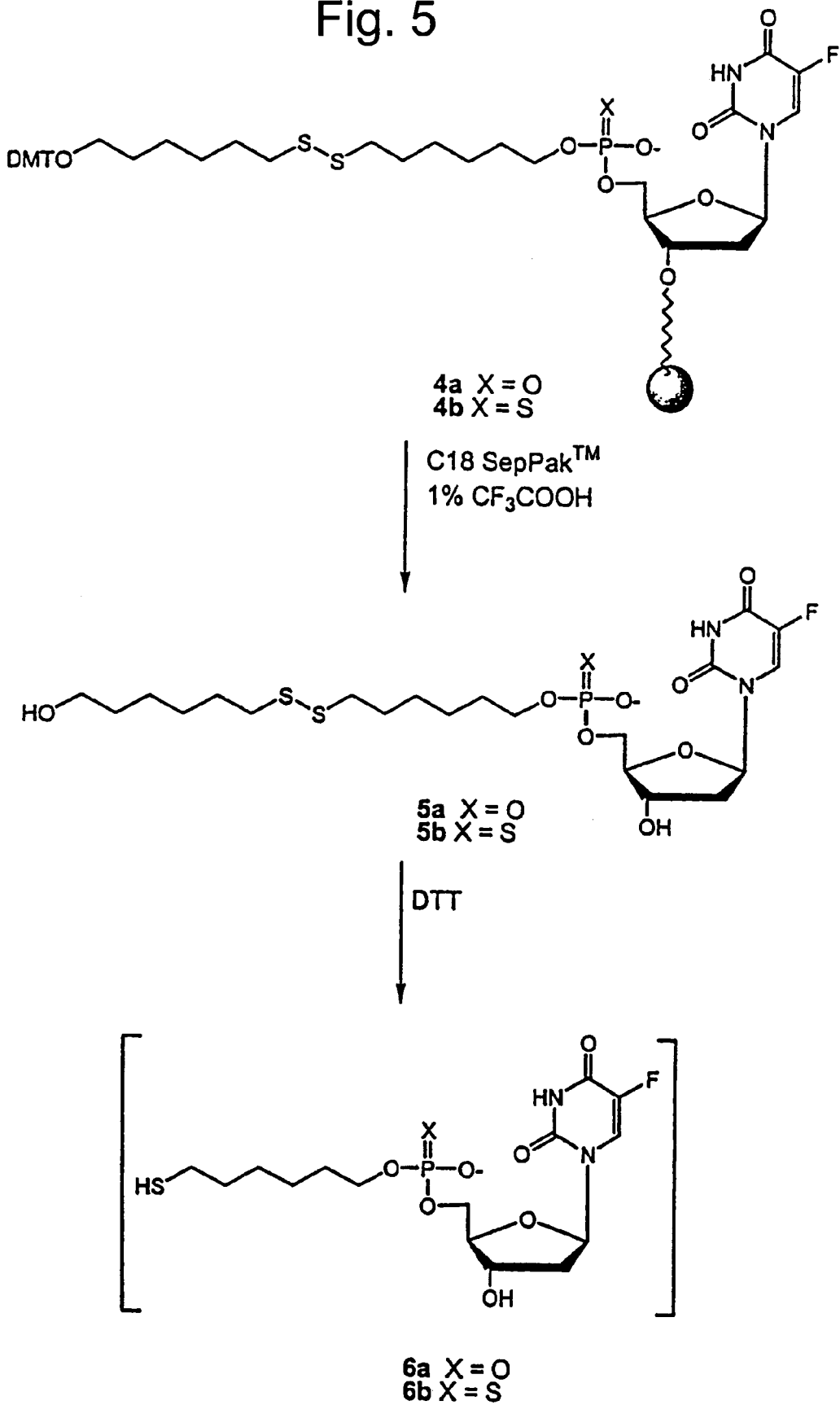
FIG. 5 depicts removal from solid support and synthesis of 5'-thiol-modified 5-fluoro-2'-deoxyuridine.

The column was then removed from the reaction port and dried under vacuum. The column's contents were then emptied into a 50 ml conical tube and the solid support was treated with a 10 ml aliquot of 0.5 M NaOH in 1/1 (v/v) $CH_3OH/H_2O$ for 3 hrs, after which the solution was brought to neutral pH (pH 7) with 20 ml of 0.5 M sodium phosphate solution (pH 5.8). This neutralized solution was then diluted to 70 ml with distilled, de-ionized $H_2O$ and applied to a classic reversed-phase C18 SepPak™ cartridge (Waters, Inc.). Prior to sample addition, the column was pre-equilibrated with $CH_3OH$ (10 ml), 50% (v/v) $CH_3CN$ in $H_2O$, and then 10 ml of $H_2O$. The column was washed with $H_2O$ (20 ml), followed by 25 ml of 5% $CH_3CN$ in $H_2O$. The column was then returned to $H_2O$ (25 ml) and a 1% aqueous solution of trifluoroacetic acid (20 ml) was used to de-tritylate. The column rapidly changed to orange in color and the flow was then stopped for 10 min. to allow for complete removal of this protecting group. Sodium phosphate (1 ml, pH 5.8, 0.5 M solution) was used to increase the pH, followed by an $H_2O$ wash (20 ml). The product (5a and 5b, FIG. 5) was then eluted with 50% $CH_3CN$ in $H_2O$. This fraction was then analyzed by reversed-phase HPLC and quantitated by UV spectrophotometrically, $\lambda_{max}$ 268 nm, $\lambda_{268}$ 5280 $M^{-1}cm^{-1}$; $A_{268}$ 0.02/20 μl; final yield is 5.67 μmoles of 5a (FIG. 5). HPLC analysis of 5a (FIG. 5): elution time 24 min (5a, FIG. 5) using a linear gradient of $CH_3CN$ in 50 mM sodium phosphate (pH 5.8) (2%→50% $CH_3CN$ in 30 min).

Example 2

This example illustrates the preparation of thiol-modified mononucleotide (FIG. 5).

The reduction of the disulfide moiety to the thiol was effected by the treatment of the 5'-disulfide-containing compound with DTT. Thus, 16 O.D.$_{268}$ (1.0 μmole) disulfide oligomer in 330 μl $H_2O$ was treated with 0.25 M sodium phosphate solution, de-gassed (pH 8). To this solution, 50 μl of freshly prepared and degassed 1 M DTT solution in $H_2O$ were added. The mixture was incubated at 37° C. for 2 hrs. Quantitative reduction was confirmed by reversed-phase HPLC analysis, which showed that the thiol-modified mononucleotide (elution time: 15.4 min for the phosphodiester-linked derivative (6a, FIG. 5) and 17.4 min for the phosphorothioate-linked derivative (6b, FIG. 5)) compared to 20.4 min for the parent disulfide phosphodiester-linked oligomer and 24 min for the parent disulfide phosphorothioate-linked oligomer) using a linear gradient of $CH_3CN$ in 50 mM sodium phosphate (pH 5.8) (2%→50% $CH_3CN$ in 30 min). The reduced product was then purified on a Sephadex G-10 column (1.0×90 cm, column void volume ($V_0$): 35 ml) to remove DTT and salts. Column packing and subsequent sample elution were effected by the use of degassed 20% ethanol-water. The fraction containing the pure thiol oligomer was used immediately in the next reaction to minimize unwanted oxidation.

Example 3

This example illustrates the synthesis of SMCC-YEE (ahGalNAc)$_3$.

About 1-2 μmole of YEE(ahGalNAc)$_3$ (see, e.g., Lee, et al., *Glycoconjugate J.*, 4, 317-328 (1987)) was dried into a 1 ml glass Reacti-vial. To this solution, anhydrous DMSO (250 μl) and anhydrous DIPEA (3 μl) were added. The solution was then treated with 150 μl of a solution containing vacuum-dried SMCC (6 mg) in anhydrous DMSO. The mixture was vortexed briefly and left standing at room temperature for 2 hrs. Analysis by reversed-phase C18 HPLC indicated complete conversion of the starting YEE (ahGalNAc)$_3$ (elution time: 6.6 min) to the desired product SMCC-YEE(ahGalNAc)$_3$ (elution time: 10.1 min). The reaction mixture was then diluted to 10 ml with 50 mM sodium phosphate (pH 5.8) containing 2% $CH_3CN$ and was loaded onto a Sep-Pak cartridge. The cartridge was washed with 10 ml of 50 mM sodium phosphate (pH 5.8) containing 2% $CH_3CN$, and the product was eluted with 10 ml of 25% $CH_3CN/H_2O$. The product was concentrated under reduced pressure in a Speed-vac and was further purified on a semi-preparative reversed-phase C18 column. Fractions containing SMCC-YEE(ahGalNAc)$_3$ as identified by HPLC and UV spectroscopic analyses were pooled and de-salted on a SepPak™. Final yield of product: 1.89 O.D.$_{276}$ or 1.35 μmole.

Example 4

This example illustrates the syntheses of SMCC-YEE (ahGalNAc)$_3$-containing mononucleotides (7a and 7b, FIG. 6).

Phosphodiester-linked mononucleotide conjugate (po 1-mer) (7a, FIG. 6)

Figure 7:
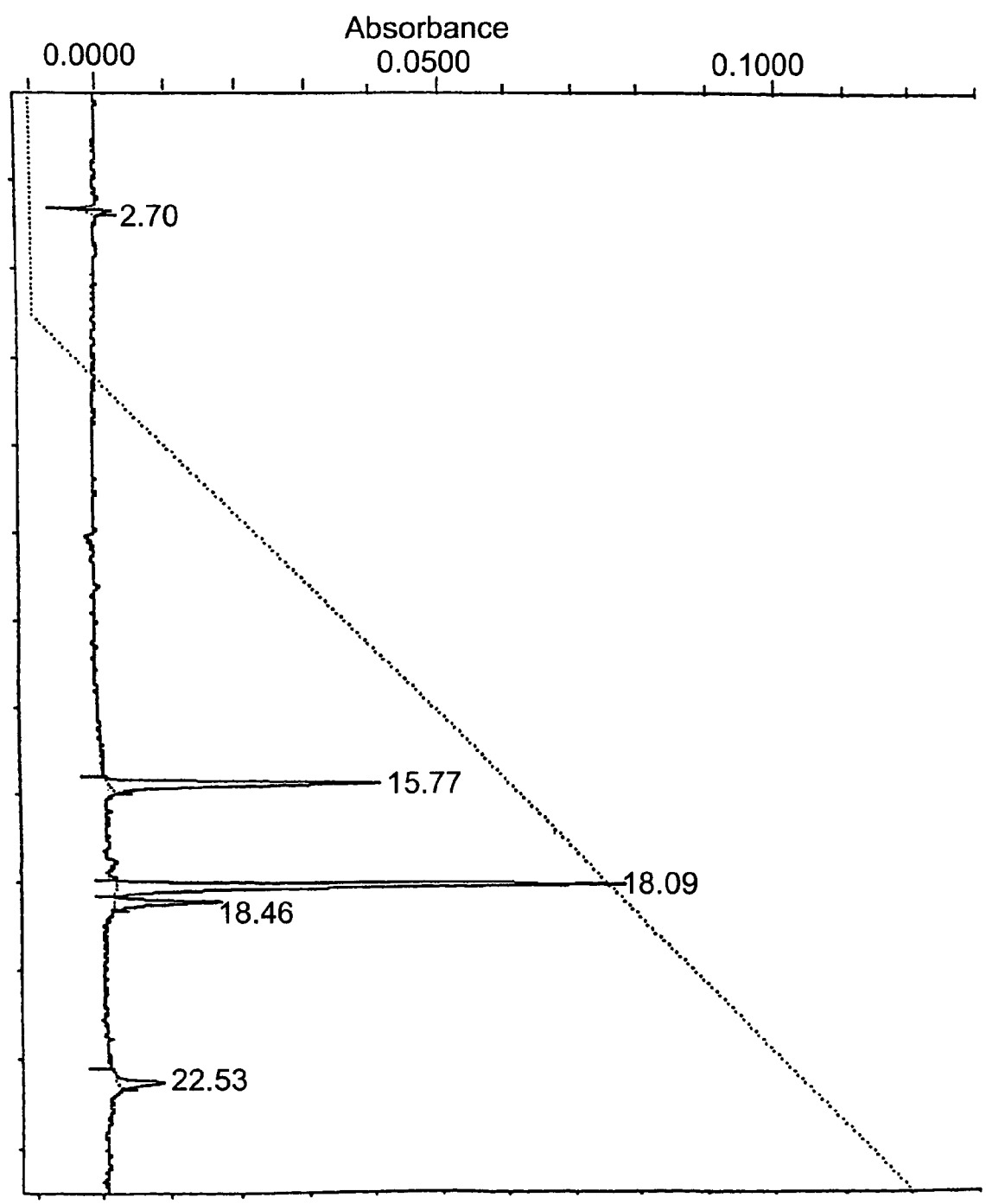
FIG. 7 depicts an HPLC analysis of crude phosphodiester mononucleotide or analogue thereof (po 1-mer) conjugation reaction mixture.

The G-10 fraction containing pure thiol oligomer (6a, FIG. 6) was mixed with an aqueous 50% $CH_3CN$ solution of SMCC-YEE(ahGalNAc)$_3$ (1.8 μmoles) (5 ml) and 5 ml of $N_2$-degassed 0.25 M sodium phosphate (pH 7) immediately after it was collected. The mixture was then concentrated to three-quarters volume in a Speed-Vac™ (Savant) and sealed tight for 24 hrs to allow conjugation to go to completion. Analysis of the crude reaction mixture by reversed-phase HPLC, using a linear gradient of $CH_3CN$ in 50 mM sodium phosphate (2%→50% $CH_3CN$ in 30 min) showed three compounds, i.e., compound #1 eluting at 15.77 min, compound #2 eluting at 18.09 min, and compound #3 eluting at 18.46 min (FIG. 7). The crude reaction mixture was further concentrated to ~1 ml and applied to a G-15 Sephadex column (1.0×43 cm; packed with 20% ethanol in $H_2O$). Elution of the column with 20% ethanol in $H_2O$ provided a mixture containing compound #1 and compound #2, the product, as identified after HPLC separation and mass spectrometric analysis. Final purification was accomplished by reversed-phase HPLC, using a linear gradient of $CH_3CN$ in 50 mM sodium phosphate (pH 5.8) (2%→50% $CH_3CN$ in 30 min). The purified material was then diluted with $H_2O$ and de-salted using a reversed-phase SepPak™ (Waters, Inc.), yielding 398 nmoles. Final confirmation of the conjugate was accomplished using MALDI mass spectrometry (Scripps Research Institute); high resolution mass spectrum (MALDI), m/z 2051.859 $M-H^+2+Na^+$. ($C_{88}H_{139}FN_{12}Na_2O_{35}PS^+$ requires 2051.870).

Phosphorothioate-linked mononucleotide conjugate (ps 1-mer) (7b, FIG. 6)

Figure 8:
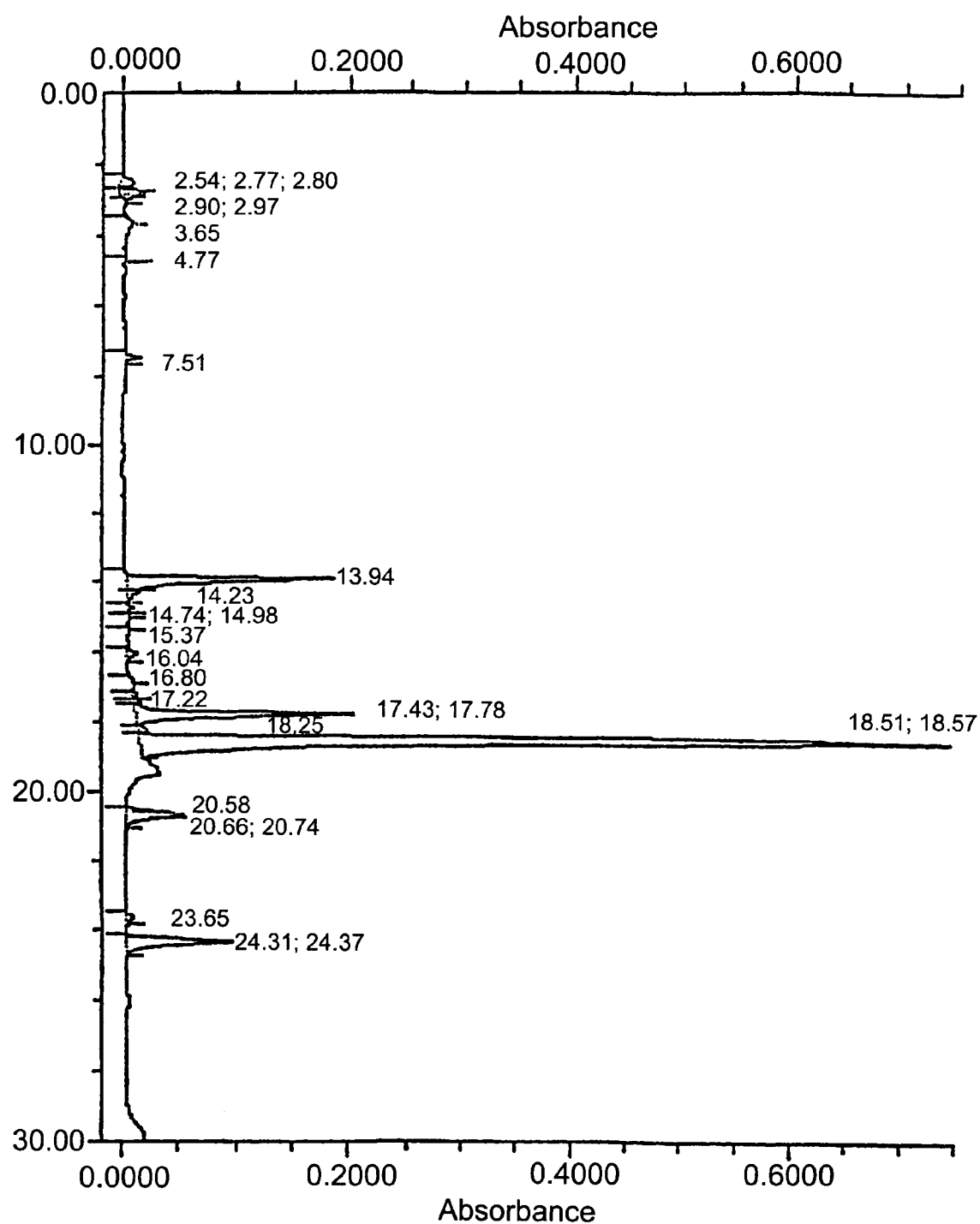
FIG. 8 depicts an HPLC analysis of crude phosphothioate mononucleotide or analogue thereof (ps 1-mer) conjugation reaction mixture.

The G-10 fraction containing pure thiol oligomer (6b, FIG. 6) was mixed with an aqueous 50% $CH_3CN$ solution of SMCC-YEE(ahGalNAc)$_3$ (1.8 µmoles) (5 ml) and 5 ml of $N_2$-degassed 0.25 M sodium phosphate (pH 7) immediately after it was collected. The mixture was then concentrated to three-quarters volume in a Speed-Vac™ (Savant) and sealed tight for 24 hrs to allow conjugation to go to completion. Analysis of the crude reaction mixture by reversed-phase HPLC, using a linear gradient of $CH_3CN$ in 50 mM sodium phosphate (2%→50% $CH_3CN$ in 30 min), showed three compounds, i.e., compound #1 eluting at 13.94 min, compound #2 eluting at 17.78 min, and compound #3 eluting at 18.57 min (FIG. 8). The crude reaction mixture was further concentrated to ~1 ml and applied to a G-15 Sephadex column (1.0×43 cm; packed with 20% ethanol in $H_2O$). Elution of the column with 20% ethanol in $H_2O$ provided a mixture containing compound #1 and compound #3, the product, as identified after HPLC separation and mass spectrometric analysis. Final purification was accomplished by reversed-phase HPLC, using a linear gradient of $CH_3CN$ in 50 mM sodium phosphate (pH 5.8) (2%→50% $CH_3CN$ in 30 min). The purified material was then diluted with $H_2O$ and de-salted using a reversed-phase SepPak™ (Waters Inc.), yielding 623 nmoles. Final confirmation of the conjugate was accomplished using MALDI mass spectrometry (Scripps Research Institute); high resolution mass spectrum (MALDI), m/z 2067.8529. $M-H^++2Na^+$. ($C_{88}H_{138}FN_{12}Na_2O_{34}PS_2^+$ requires 2067.8475).

Example 5

This example describes the 3'-terminal radiolabeling procedure for all YEE(ahGalNAc)$_3$-derived conjugates used in subsequent biological experiments (e.g. cellular uptake and in vivo biodistribution).

Reaction mixtures (355 µl final volume) contained 20 nmoles of po 1-mer conjugate (7), 30 µl of 10×TdT buffer, 30 µl of 4 mM $CoCl_2$, 50 µl of [$^{35}$S] αS—ATP (10 µCi/µl, 500 µCi total), and 500 units (25 µl) of TdT. This mixture was incubated at 37° C. for 16 hrs, then cooled to room temperature and diluted with 400 µl of 0.5 M sodium phosphate (pH 5.8). This solution was allowed to incubate at room temperature for 1 hr. Purification of the product was accomplished through size-exclusion gel filtration (G-15 Sephadex column, 1.0×43 cm with 20% ethanol in $H_2O$). The fraction corresponding to the largest molecular weight was analyzed by UV spectrophotometry and then by scintillation counting; $A_{268}$: 0.036/20 µl; total volume of fraction: 1.9 ml; cpm/20 µl: 1372200; total cpm: 1.30×10$^8$; total mass: 12.95 nmoles; specific activity: 4.58 µCi/nmole.

Example 6

This example describes the synthesis of the 5-fluoro-2'-deoxyuridine 5'-monothiophosphate (8, FIG. 9).

A 15-µmole column was prepared using 0.342 g (40 µmole/g loading capacity) of the Universal-Q CPG (1, FIG. 9) and placed in one of the two reaction ports of a Millipore Expedite DNA/RNA synthesizer. Specifically, a $CH_3CN$ solution containing the 5-fluoro-2'-deoxyuridine synthon (2, FIG. 9) (0.25 g in 5 ml of $CH_3CN$) was placed in the "T" bottle, and the C6 disulfide phosphoramidite synthon was placed in the "5" bottle. The automated synthesis was carried out sequentially (from the 3'→5'-end), and entailed the reaction of the 5-fluoro-2'-deoxyuridine phosphoramidite synthon (2, FIG. 9) with the solid support followed by treatment with the "Chemical Phosphorylation I" synthon. For the phosphodiester-linked compound, the standard oxidizing solution (3% $I_2$ in a solution of tetrahydrofuran/pyridine/$H_2O$) (Glen Research Inc.) was used. The Beaucage reagent, 3H-1,2-benzodithiole-3-one,1,1-dioxide (Glen Research Inc.) was substituted for the oxidizer solution to effect sulfurization of the phosphite to give the phosphorothioate according to standard established procedures. This reagent was used at a concentration of 100 mg reagent in 10 ml of anhydrous $CH_3CN$. Standard oxidation times were followed (30 sec for both phosphodiester- and phosphorothioate-linked compounds). The final 5'-DMT was removed in order to facilitate purification.

The column was then removed from the reaction port and dried under vacuum. The column's contents were then emptied into a 120 ml cylindrical tube and the solid support was treated with a 10 ml aliquot of 0.5 M NaOH in 1/1 (v/v) $CH_3OH/H_2O$ for 3 hrs, after which the solution was brought to neutral pH (pH 7) with 40 ml of 0.5 M sodium phosphate solution (pH 5.8). This neutralized solution was then diluted to 100 ml with distilled, de-ionized $H_2O$ and applied to a 20 cc (5 g) reversed-phase C18 SepPak™ cartridge (Waters, Inc.). Prior to sample addition, the column was pre-equilibrated with $CH_3OH$ (30 ml), 50% (v/v) $CH_3CN$ in $H_2O$, and then 30 ml of $H_2O$. The column was washed with $H_2O$ (30 ml), followed by 20-40 ml of 5% $CH_3CN$ in $H_2O$. The column was then returned to $H_2O$, and the product was then eluted with 50% $CH_3CN$ in $H_2O$. This fraction was then analyzed by reversed-phase IPLC and quantitated by UV spectrophotometrically, $\lambda_{max}$ 268 nm, $\lambda_{268}$ 5280 $M^{-1}cm^{-1}$; $A_{268}$ 0.067/100 µl; final yield 62.3 O.D.; 11.8 µmoles. HPLC analysis: elution time 2.6 min using an isocratic gradient of 2% $CH_3CN$ in 50 mM sodium phosphate (pH 5.8).

Example 7

This example describes the studies used to assess the serum stability of po 1-mer conjugate (7a, FIG. 6).

Studies were carried out at physiological conditions. The analyses were accomplished using reversed-phase HPLC and PAGE methods. The raw data are presented in table format (Tables 1, 2 and 3). The serum half-life calculated is $t_{1/2}=1/k$ (0.693), derived from the $[A]=[A_0]e^{-kt}$, where $[A_0]$ is the original amount of substrate, $[A]$ is the measured substrate level, t is time (min), and k is the first-order rate constant.

HPLC Analytical Methods (a) Reaction Conditions: 50 µl of human serum were added to 24 nmoles of HPLC purified po 1-mer Conjugate and incubated at 37° C. for allotted time periods (0 min, 60 min, 180 min, 360 min). Column 1: flow 1.0 ml/min, Rainin MicroSorb C18 reversed-phase column HPLC gradient: 100% $NH_4OAc$ for 10 min, then 0→100% $CH_3CN$ in 25 min. (0.1 M $NH_4OAc$) (Table 1).

TABLE 1

| Time (min) | Trial 1 Peak Area | Trial 2 Peak Area | Average Peak Area | Standard Deviation Peak Area |
|---|---|---|---|---|
| 0 | 17.64988 | 17.92 | 17.78494 | 0.191003684 |
| 60 | 15.10503 | 12.42582 | 13.76543 | 1.894487559 |
| 180 | 9.35569 | 10.9908 | 10.17325 | 1.156197369 |
| 360 | 11.4 | | 11.4 | 0 |

$y = 15.429e^{-0.0012x}$
$t_{1/2} = 577.5$ min or 9.6 hrs (b) Reaction Conditions: 100 µl of human serum were added to 20 nmoles of HPLc purified po 1-mer Conjugate and incubated at 37° C. for allotted time periods (0 min, 15 min, 60 min, 120 min, 240 min). HPLC gradient: 100% Buffer A (0.05M $NaxPO_4$ (pH 5.8) in 2% $CH_3CN$) for 5 min, then 2% $CH_3CN$ to 50% $CH_3CN$ over the next 20 min. Column 2: flow 4.7 ml/min, Rainin Semi-Preparative C18 reversed-phase column (10 mm i.d.×250 mm L) (Table 2).

TABLE 2

| time (min) | Trial 1 Peak area | Trial 2 Peak area | Trial 3 Peak area | Average Peak area | Standard Deviation Peak area |
|---|---|---|---|---|---|
| 0 | 13.07 | 12.68 | 14.97 | 13.57333 | 1.225166655 |
| 15 | 14.86 | | | 14.86 | 0 |
| 60 | 14.21954 | | | 14.21954 | 0 |
| 120 | 11.95526 | | | 11.95526 | 0 |
| 240 | 9.72692 | | | 9.72692 | 0 |

$y = 14.698e^{-0.0017x}$
$t_{1/2} = 407$ min or 6.79 hrs

Page Analysis

Reaction Conditions: 2 µl of human serum were added to 200,000 cpm of dry $^{35}S$ labeled po 1-mer conjugate. Radiolabeled conjugate was incubated at 37° C. in the presence of this serum for the allotted time periods (15 min, 30 min, 60 min, 120 min, 240 min). The reaction mixture was diluted with 2 µl of $H_2O$, then 4 µl of loading buffer. The degradation pattern was observed through autoradiography of a 20% polyacylamide gel (0.75 mm) run at 800 V for 90 min. Bands were quantified through the use of a Fujix BAS 2000 Phosphorimager (Table 3).

TABLE 3

| Time (min) | Pixel Area | Normalized Area | Standardized Area |
|---|---|---|---|
| 0 | 42.57 | 0 | 1 |
| 15 | 57.43 | 0.1486 | 0.8514 |
| 30 | 66.61 | 0.2404 | 0.7596 |
| 60 | 76.92 | 0.3435 | 0.6565 |
| 120 | 81.57 | 0.39 | 0.61 |
| 240 | 80.13 | 0.3756 | 0.6244 |

$y = 0.8387e^{-0.0016x}$
$t_{1/2} = 433$ min or 7.2 hrs
Overall average $t_{1/2} = 7.8$ hrs for Tables 1-3.

Example 8

This example demonstrates the cellular uptake of the 5FU 1-mer conjugate (either YEE(ahGalNAc)$_3$-SMCC-psFU (phosphothioate-linked[ps] conjugate) or YEE (ahGalNAc)$_3$-SMCC-poFU (phosphodiester-linked [po] conjugate)).

Hep G2 cells were passaged into 2 cm$^2$ wells and grown in RPMI 1640 medium, which was supplemented with L-glutamine (10-040, CV) to a density of $0.3 \times 10^6$ to $0.4 \times 10^6$ cells per well (48-well cluster plate, Costar, Cambridge, Mass.). The maintenance medium was aspirated and the cells were incubated at 37° C. with 0.2 ml medium that contained 2% FCS and was made 1 µM in [5'-$^{35}$S]-labeled YEE(ahGalNAc)$_3$-SMCC-psFu (phosphothioate-linked[ps] conjugate) or YEE(ahGalNAc)$_3$-SMCC-poFU (phosphodiester-linked [po] conjugate). Then, an aliquot of the medium was saved for scintillation counting and the remainder of the medium aspirated from the well. The cells were washed with D-PBS (2×0.5 ml), treated with 0.25% trypsin (37° C., 2 minutes; trypsin prepared in HBSS with 1.0 mM EDTA) and suspended in fresh growth medium containing 10% FCS. The suspended cells were layered over silicon oil (0.5 ml) in a 1.7 ml conical microcentrifuge tube and pelleted by centrifugation at 14,000 rpm (12,000 g) for 30 seconds. The supernatant was carefully decanted and the cell pellet was lysed with 100 µl of a solution containing 0.5% NP 40, 100 mM sodium chloride, 14 mM Tris/HCl and 30% acetonitrile. The amount of radioactivity, and by inference the amount of neoglycoconjugate or oligomer associated with the cell lysate, was determined by scintillation counting.

The association of the ps- and po-linked, 5 FU-containing neoglycoconjugate with Hep G2 cells was examined in order to demonstrate and compare uptake in cells of hepatic origin. Initially, the stability of the two neoglycoconjugates was assessed in RPMI 1640+10% FCS. Both the ps-linked and po-linked 1-mer conjugates were stable in media containing 10% FCS for up to 8 hrs as demonstrated by PAGE analysis. These data confirm that both conjugates demonstrate sufficient in vitro stability, such that they could be used for cellular uptake studies. In terms of cellular uptake, the po-linked conjugate at a dose of 1 µM was taken up rapidly in a progressive manner by Hep G2 cells in vitro to the extent of 24.75 pmoles/10$^6$ cells at 480 min. The rate of cellular uptake was next analyzed with respect to the administered dose of the conjugate. The administration of 1 µM po-linked conjugate resulted in the cellular uptake of 5 pmoles/million cells at 30 min. This amount doubled within the next 30 min and peaked at 25 pmoles/million cells at 480 min. Doubling the administered dose to 2 µM did not significantly enhance cellular uptake since the initial concentration of the conjugate found intracellularly and the maximum cellular uptake mimicked those of the 1 µM dose. Increasing the administered dose to 4 µM and 8 µM resulted in the maximal cellular uptake of 36 and 43 pmoles/million cells, respectively. While the administration of 4 µM conjugate led to a linear increase of conjugate uptake with respect to time, the rate at which cellular uptake occurred upon the administration of 8 µM conjugate rose sharply at 120 min. The pattern of conjugate intake did not depend on the type of linkage that the nucleotide comprised since similar patterns of cellular uptake were achieved when the conjugate was ps-linked.

When the concentration of conjugate in the medium was increased to 2 µM, 4 µM, and 8 µM, uptake increased with increasing concentration, but was not proportional to the dose. Doubling the concentration of the conjugate did not significantly increase cellular uptake, as the administration of 2 µM resulted in uptake of about 26 pmole/$10^6$ cells at 480 min. Increasing the concentration of the conjugate to 4 µM and 8 µM resulted in the maximum cellular uptake of about 36 pmoles/$10^6$ cells and 42 pmoles/$10^6$ cells, respectively, at 480 min. However, the rate of uptake was enhanced, since administration of 8 µM of the conjugate results in uptake of 35 pmoles/$10^6$ cells in only 120 min.

Cellular uptake of YEE(ahGalNAc)$_3$-SMCC-psFU by Hep G2 cells was very similar to that of the po-linked conjugate achieving 24.98 pmoles/$10^6$ cells at 480 minutes. Again, when the concentration of conjugate in the media was increased to 2 µM, 4 µM, and 8 µM, uptake increased with increasing concentration, but was not proportional to the dose.

The above data show that the uptake rates of the po- and ps-linked conjugates are essentially identical for all concentrations studied. This indicates that the interaction of the receptors on the Hep G2 cell surface with the unique ligand is responsible for the degree of cellular uptake, regardless of the chemical bonds securing "P". The fact that cellular uptake is not proportional with increasing conjugate concentration may be due to the artificial environment of the cell culture in which expression of receptors is suboptimal including those required for proliferation, during the phase of cellular proliferation required for subsequent in vitro bioefficacy testing. Nonetheless, the above experiments indicate that increasing the in vitro concentration of both neoglycoconjugates, under the conditions studied, results in an increased level of conjugate being delivered to the cell.

Example 9

This example demonstrates the effect of the present inventive conjugates on cellular proliferation.

Hep G2 cells were seeded into a 48-well plate in RPMI supplemented with 10% FCS at a density of $5\times10^4$ cells/well. Cells were then allowed to incubate at 37° C., 95% RH, 5% $CO_2$ for 24 hrs. After this incubation period, the maintainence medium was aspirated and cells were treated with various concentrations of neoglycoconjugate in 200 µl of RPMI supplemented with 10% FCS. Control wells were treated with 200 µl of RPMI+10% FCS alone. At 0, 24, 48, 72 and 96 hrs, six wells for each condition were washed twice with 0.5 ml of DPBS and treated with 0.5 ml of trypsin (0.25%; prepared in HBSS with 1.0 mM EDTA). Cell number for each condition were determined a using a Coulter electronic cell counter. In all cases, the extent of inhibition of proliferation increased as a function of time. Treatment of the Hep G2 cells with the unconjugated monomer resulted in approximately 20% inhibition of proliferation. The effect of conjugating the nucleotide analog was significant as treatment with the po-linked conjugate resulted in an initial 10% inhibition that peaked at 64%. Treatment with the ps-linked conjugate was less effective as the initial inhibition was approximately 5%, which increased to only 45% after 96 hrs. Therefore, the type of linkage that conjugates the nucleotide analog to YEE(ahGalNAc)$_3$ influences the ability to inhibit proliferation.

Hep G2 cells were treated with a 1 µM concentration of po-linked neoglycoconjugate, ps-linked neoglycoconjugate or unconjugated monomer. The average cell number for six replicate wells was determined for each treatment and an untreated control at 24, 48, 72 and 96 hrs. Treatment of Hep G2 cells with the unconjugated monomer resulted in 15-20% inhibition of proliferation as compared to the untreated control. Treatment of Hep G2 cells with the po-linked neoglycoconjugate resulted in an inhibition of proliferation of approximately 64%. In contrast, the ps-linked neoglycoconjugate administered at an identical concentration resulted in an inhibition of proliferation of about 44%.

When the concentration of either conjugate in the media was increased to 2 µM, 4 µM, and 8 µM, the inhibition of proliferation was increased relative to the 1 µM dose of the same conjugate. Thus, the inhibition induced by the ps-linked conjugate increased from 44% at a dose of 1 µm to 60% at a dose of 8 µM. Similarly, inhibition induced by the po-linked conjugate increased from 64% at a dose of 1 µm to 90% at a dose of 8 µM. Therefore, the po-linked conjugate was approximately 30% more active than the ps-linked conjugate with respect to in vitro proliferation of Hep G2 cells. The increased inhibition of proliferation was not proportional to the dose administered for either conjugate. Nonetheless, the data from the experiments described above demonstrate that the delivery of increased amounts of neoglycoconjugate result in an increasing inhibition of cellular proliferation.

Example 10

This example describes cell toxicity studies.

Hep G2 cells were seeded into a 48-well plate in RPMI supplemented with 10% FCS at a density of $5\times10^4$ cells/well. Cells were then allowed to incubate at 37° C., 95% RH, 5% $CO_2$ for 24 hrs. After this incubation period, the maintenance medium was aspirated and cells were treated with various concentrations of neoglycoconjugate in 200 µl of RPMI supplemented with 10% FCS. Control wells were treated with 200 µl of RPMI+10% FCS alone. At 0, 24, 48, 72 and 96 hrs, six wells for each condition were washed twice with 0.5 ml of DPBS and treated with 0.5 ml of trypsin (0.25%; prepared in HBSS with 1.0 mM EDTA) for 5 min at 37° C., 95% RH, 5% $CO_2$. Trypsinization was stopped by the addition of 0.5 ml of RPMI+10% FCS. The cell sample (900 µl) was then inoculated into 100 µl Trypan Blue, such that the final concentration of dye was 10%. This solution was incubated at room temperature for 5 min and a sample of 100 µl was inoculated into a hemocytometer. Three fields of 100 cells were read for each well. Cells taking up and retaining the dye were considered to be dead. Data were expressed as # viable cells/total cells counted=% viable cells.

Hep G2 cells were treated with varying concentrations of either po-linked neoglycoconjugate, or ps-linked neoglycoconjugate. Toxicity was determined via the Trypan Blue exclusion method as described above. All values were compared to that generated with untreated cells of the same origin. Overall, the degree of toxicity was related to the dose administered. At 72 hrs, the treatment of cells with 2 µM po-linked conjugate resulted in an approximate 50% decrease in viable cells whereas treatment with 8 µM led to a 75% decrease in number of viable cells. The administration of the ps-linked conjugate was less effective at decreasing the number of viable cells as compared to the po-linked conjugate, since only an approximate 25% decrease in the number of viable cells was observed at 72 hrs of treatment with 2 µM of the conjugate and an about 45% decrease was seen with 8 µM of the conjugate. In all cases, 96 hrs of treatment did not significantly change the number of viable cells as compared to those at 72 hrs, with the exception that treatment with 8 µM ps-linked conjugate further decreased the number of viable cells. This suggests that the ps-linked conjugate is less efficient at decreasing the numbers of viable cells.

Example 11

This example describes thymidylate synthetase activity in cells in the presence of po 1-mer and ps 1-mer.

A CD-1 mouse (Charles River, Wilmington, Mass.) was sacrificed and the liver removed. Approximately one gram of the tissue was subsequently washed in DPBS (Mediatech, Herndon, Va.) and placed in 3 volumes of buffer H. The tissue was then homogenized with a Dounce homogenizer and subsequently sonicated by three 15-second bursts followed by 1 min on ice. The tissue extract was then centrifuged for 10 min at 4,000 g and the resultant supernatant was spun for 20 min at 7,000 g. Three equal aliquots of this supernatant were then added to 0.9 µCi aliquots of 2'-Deoxyuridine 5'-monophosphate, diammonium salt, [5-$^3$H]. At this point, 5-Fluoro-2'-deoxyuridine 5'-monothiophosphate was added to one aliquot, 5-Fluoro-2'-deoxyuridine 5'-monophosphate was added to a second aliquot, and one aliquot was left untreated. The three samples were incubated at 37° C. for 30 min and precipitated with charcoal. The resultant supernatant was centrifuged at 1,600 g for 10 min. Aliquots of each sample were then counted using a Beckman scintillation counter. Percent (%) inhibition is expressed as follows:

$$\frac{\text{control value} - \text{treated value}}{\text{control value}}.$$

These assays determined the ability of either 10 nM FdUMP (phosphodiester substrate) or FdUMPS (phosphorothioate substrate) to inhibit thymidylate synthetase (TS) activity. The objective of this assay was to determine the ability of TS to convert [5-$^3$H]-dUMP to $^3$H-H$_2$O. As shown in Table 4 below, FdUMP displayed approximately twice the biological activity as FdUMPS.

TABLE 4

Comparison of FdUMP and FdUMPS monomers on their ability to inhibit TS catalytic activity.

Percent Inhibition of Thymidylate Synthetase Activity

| Assay [dUMP] | 10 nM FdUMP | 10 nM FdUMPS |
|---|---|---|
| 10 µM dUMP | 28% | 13% |
| 1 µM dUMP | 48% | 27% |

Example 12

This example illustrates the effect of po 1-mer on Hep G2 cellular proliferation due to the enhanced inhibition of thymidylate synthase (TS) activity.

Thymidylate synthase inhibition results in insufficient thymidylate levels for DNA replication and can lead to intracellular signaling processes that ultimately lead to cell death. The activity of this paramount enzyme was determined based on the methods of Keyomarsi et al. (*J. Biol. Chem.*, 268, 15142-15149 (1993)). Briefly, 10$^5$ Hep G2 or TSU cells were grown in culture for 48 h and then the medium was made to a concentration of 1 µM with either po 1-mer or unconjugated 5FdU. At regular intervals (24 hrs, 48 hrs, 72 hrs and 96 hrs) after treatment, the medium was removed and replaced with medium containing deoxyuridine/[$^3$H]-deoxyuridine mixtures. Cells were incubated at 37° C. for 30 min. Cell medium was then removed and precipitated with charcoal. The supernatant was then counted to determine the presence of [$^3$H]-H$_2$O. The measurable release of [$^3$H] as [$^3$H]-H$_2$O from deoxyuridine, 5'-monophosphate (dUMP) substrate reflects thymidylate synthase activity.

In this regard, treatment of Hep G2 cells with po 1-mer at a concentration of 1 µM resulted in a progressive inhibition of the release of [$^3$H]-H$_2$O, indicative of severely depressed TS activity. In this case, TS activity was reduced by 60% at 96 hrs post treatment. In contrast, unconjugated 5FdU reduced TS activity by approximately 20% in the same time period. These data correlated well with the effects of the treatments on inhibition of cell growth. The inhibition of TS activity induced by po 1-mer was cell-specific as no inhibitory effect was observed in TSU carcinoma cells upon treatment with po 1-mer. Furthermore, the viability of these cells was not affected when the cells were treated with the po 1-mer conjugate.

Example 13

This example illustrates biodistribution experiments in order to determine the in vivo localization of po 1-mer.

For these studies, male CD-1 mice were i.v. injected via the tail vein with either [3'-$^{35}$S]-radiolabeled po 1-mer or [6-$^3$H]-unconjugated 5FdU. At the appropriate time interval, the mice were sacrificed, the organs excised, then solubilized. The amount of radioactivity associated with each organ was determined by scintillation counting and corrected for efficiency. Standard CD-1 mice were used in these initial experiments to ascertain baseline distribution in normal mice, whereas subsequent bioefficacy experiments will use CD-1 nude mice. The result of these experiments was that po 1-mer rapidly and specifically localized to the liver. Fifty-seven percent of the injected po 1-mer localized to the liver within 15 min as opposed to less than 10% of the injected unconjugated 5FdU (Table 5). Even at 60 min post-injection, 25% of po 1-mer was found in the liver (Table 6). Eight hours after injection, virtually no po 1-mer was localized to the liver. The po 1-mer conjugate did display a significant early accumulation in the muscle and subsequent accumulation in the intestinal tract (Table 5). The existence of various beta-galactose lectins in the muscle could to some extent compete for the GalNAc residues, which would account for this early accumulation (Barondes, et al., *J. Biol. Chem.*, 269, 20807-20810 (1994); see also Poirier et al., *Development*, 115, 143-155 (1992)). However, since the proliferative index of muscle cells is low, the rendering of the delivered nucleotide analogue to active metabolites should be minimal. The accumulation of the radiolabel in the intestines at later time points could be due to enterohepatic redistribution of 5FU metabolites. Nevertheless, a nucleotide is initially being delivered to the liver cells, which carries a charged phosphate, thereby preventing it from being eliminated by the cell. Subsequent anabolic/catabolic processes might lead to redistribution of radioactive metabolites, complicating distribution analysis. Although enterohepatic recycling is a factor to be considered, its importance has been questioned due to the low percentage of 5FU metabolites excreted by the biliary route (Young et al., *Nuklearmedizin*, 21, 1-7 (1982)). Another possible explanation for the non-hepatic distributions can be the use of an uncharacterized label, due to rapid intracellular dissociation of the radiolabel from the conjugate with subsequent non-specific accumulation of the label. Despite the above-mentioned caveats, these experiments clearly demonstrate that po 1-mer delivers its payload in a rapid and specific manner to the liver of mice.

TABLE 5

Relative Percentages of 5FU 1-mer in the Organs of CD-1 Normal Mice Which Resulted from the Tail Vein i.v. Administration of [3'-$^{35}$S]-labeled PO 1-mer.

| ORGAN | 15 MIN | 30 MIN | 60 MIN | 120 MIN | 240 MIN | 480 MIN |
|---|---|---|---|---|---|---|
| LIVER | 57.61 ± 9.04 | 50.93 ± 2.44 | 24.60 ± 5.51 | 9.93 ± 1.92 | 3.29 ± 0.31 | 2.87 ± 0.29 |
| KIDNEY | 0.96 ± 0.12 | 1.07 ± 0.17 | 2.50 ± 1.34 | 1.52 ± 0.14 | 0.56 ± 0.14 | 0.44 ± 0.11 |
| SPLEEN | 0.12 ± 0.01 | 0.368 ± 0.51 | 0.19 ± 0.12 | 0.17 ± 0.037 | 0.33 ± 0.43 | 0.07 ± 0.012 |
| MUSCLE | 3.80 ± 1.69 | 7.87 ± 3.55 | 10.33 ± 8.85 | 5.54 ± 3.96 | 5.48 ± 0.7 | 4.58 ± 3.9 |
| SM INT | 2.56 ± 3.58 | 4.00 ± 5.01 | 4.26 ± 14.94 | 5.77 ± 2.4 | 3.31 ± 4.74 | 3.7 ± 3.84 |
| LG INT | 1.02 ± 0.34 | 4.217 ± 5.93 | 2.45 ± 2.16 | 0.95 ± 0.032 | 3.29 ± 0.31 | 7.94 ± 0.65 |
| LUNGS | 0.42 ± 0.13 | 0.35 ± 0.16 | 0.77 ± 0.53 | 0.49 ± 0.85 | 3.29 ± 0.31 | 0.33 ± 0.055 |
| HEART | 0.168 ± 0.02 | 0.18 ± 0.11 | 0.33 ± 0.19 | 0.17 ± 0.016 | 3.29 ± 0.31 | 0.081 ± .006 |
| BLOOD | 2.19 ± 1.57 | 1.3 ± 0.15 | 3.13 | 2.7 | 3.29 ± 0.31 | 0.81 ± 0.47 |
| BLADDER | 3.05 ± 0.33 | 0.33 ± 0.3 | 6.97 ± 9.8 | 6.85 ± 5.97 | 3.29 ± 0.31 | 4.23 ± 5.83 |

TABLE 6

Relative Percentages of 5FdU in the Organs of CD-1 Normal Mice Which Resulted from the Tail Vein i.v. Administration of [6-$^{3}$H] Unconjugated 5FdU.
% INJECTED DOSE - 5FdU

| ORGAN | 15 MIN | 30 MIN | 60 MIN | 120 MIN | 240 MIN | 480 MIN |
|---|---|---|---|---|---|---|
| LIVER | 9.56 ± 3.83 | 8.8 ± 1.23 | 4.35 ± 1.35 | ND | 3.97 ± 0.37 | 1.25 ± 0.33 |
| KIDNEY | 0.42 ± 0.28 | 0.38 ± 0.3 | 0.84 ± 0.31 | | 0.44 ± 0.12 | 0.13 ± .044 |
| SPLEEN | 0.11 ± 0.044 | 0.19 ± 0.26 | 0.57 ± 0.18 | | 0.38 ± 0.04 | 0.09 ± 0.05 |
| MUSCLE | 9.29 ± 4.9 | 3.43 ± 1.06 | 22.84 | | 46.56 | 7.9 ± 1.64 |
| SM INT | 0.7 ± 0.04 | 0.61 ± 0.36 | 3.57 ± 1.3 | | 4.19 ± 1.18 | 1.37 ± 0.7 |
| LG INT | 1.09 ± 0.25 | 0.37 ± 0.19 | 1.04 ± 0.2 | | 1.61 ± 0.59 | 0.35 ± 0.09 |
| LUNGS | 0.17 ± 0.07 | 0.05 ± 0.006 | 0.98 ± 0.3 | | 1.03 ± 0.39 | 0.08 ± 0.04 |
| HEART | 0.21 ± 0.13 | 0.03 ± .004 | 0.28 ± 0.11 | | 0.32 ± 0.10 | 0.06 ± .02 |
| BLOOD | 0.03 ± 0.02 | .008 ± .0025 | .007 ± .0023 | | 0.56 ± 0.28 | 0.23 ± 0.14 |
| BLADDER | 0.91 ± 0.07 | 2.3 ± 1.58 | 2.99 ± 1.01 | | 0.010 ± .015 | .001 ± .0006 |

ND is not determined.

Example 14

The example illustrates an assay on po 1-mer for both hepatic and systemic toxicity in CD-1 mice.

Mice have previously been used as in vivo models for 5FU drug testing in the following manner (Ain et al., *J. Surg. Res.*, 57, 366-372 (1994); Wang et al., *Cancer Res.*, 50, 869s-872s (1990)). The plasma profiles, induced toxicities and pharmacokinetics of 5FU in mice are similar to those observed in humans (Wagner et al., *Cancer Res.*, 46, 1499-1506 (1986)). Both po 1-mer and 5FdU were administered on a clinically relevant regimen of 4 weekly bolus injections via the tail vein (Anfield et al., *Cancer*, 39, 34-40 (1977)). The starting doses of 10 mg/kg and 15 mg/kg were determined by extrapolation of the in vitro data. One week after each injection, a cohort of animals (6 animals/dose/treatment) was sacrificed. Blood and liver samples were collected from each animal and assayed for hepatic and systemic toxicities. The blood sample analyses included a Superchem panel and a total blood count. The Superchem panel assayed blood levels of glucose, urea nitrogen (BUN), creatinine, total protein, albumin, both conjugated and unconjugated bilirubin, triglycerides, SGOT, SGPT, triglycerides, CPK, alkaline phosphatase, and peripheral blood differentials. Total blood counts were analyzed for hematocrit, as well as both red and white blood cell counts. Liver samples were subjected to histological analysis in order to determine changes in morphology, architecture and increase in necrotic tissue as compared to the controls. Any acute or sustained increases in blood counts or serum components indicative of organ damage in comparison with the untreated control was taken to be indicative of a toxic response. In addition, the weights of each cohort were recorded throughout the treatment period as an indication of their clinical condition.

po 1-mer at Weekly 10 mg/Kg Dose Level.

Results from these experiments indicated a mild toxicity associated with each dose. Physically, food and water consumption were normal, while weight gain over a four week period was progressive and similar to the saline-treated control mice. However, the po 1-mer treatment of the mice at the dose level of 10 mg/kg resulted in a significantly depressed white blood cell count and mild hypochromic anemia. The analysis of the blood chemistry resulted in SGPT levels at the top of the reference range and significantly increased SGOT levels. These results are summarized in Table 7. In addition, lactate dehydrogenase levels and serum potassium levels were increased indicating the loss of cell cytoplasm and excess destruction of cells. Elevated urea nitrogen (BUN) and sodium levels, as well as decreased chloride calcium levels, characteristic of mild kidney disturbance, were also detected. However, increased total bilirubin and gamma-glutamyl transferase (GT) levels, an indication of major liver damage, were not observed. Histological analysis did not reveal any pathological changes past mild hepatocellular swelling. In a clinical sense, the mice displayed no adverse impact of the treatment. The toxic effects of this dose appeared transient. When treatment was stopped for two weeks, all blood values began to return to the reference range and the hepatocellular swelling subsided (week 6 in Table 7).

po 1-mer at Weekly 15 mg/Kg Dose Level.

Results of the toxicity testing of po 1-mer (15 mg/kg) were similar to those seen with 10 mg/kg dosage level.

These data are presented in Table 8. Complete blood count results revealed a significantly depressed white blood cell count, mild hypochromic anemia and mild thrombocytopenia. Blood chemistry results demonstrated SGPT levels at the top of the reference range and significantly increased SGOT levels indicative of some disturbance to hepatocytes. In addition, lactate dehydrogenase levels and serum potassium levels were increased, indicating the loss of cell cytoplasm. As before with the 10 mg/kg dose, increased total bilirubin and gamma-GT levels indicative of major liver damage were not observed. Moreover, histological analysis revealed mild hepatocellular swelling and limited subcapsular fibrosis in one mouse. In a clinical sense, the mice displayed no adverse impact of the treatment. Food and water consumption were normal and, while weight gain was somewhat less than the untreated control mice, the rate of gain was still progressive. The effect of cessation of treatment upon recovery is currently being analyzed. The data from these experiments indicated that the toxicity of po 1-mer was mild at best and permitted testing to be advanced to bioefficacy considerations.

New York, N.Y., pp. 97-104) and Keyomarsi et al. ((1988), *J. Biol. Chem.*, 263:14402-14409). Through these measurements, TS inhibition effects of each 5FdUMP or leucovorin residue can be determined. Cellular component quantitations will be performed in triplicate so statistical significance can be determined using student's paired t-test method.

TS Levels

Thymidylate synthetase levels are quantified by titration of the active sites with [$^3$H]-FdUMP in the presence of excess folate (5,1 0-methylene tetrahydrofolate, 5,10-CH$_2$-H$_4$PteGlu). Exponentially growing cells are exposed to drugs continuously under conditions monitored for humidity and CO$_2$ content in media supplemented with 10% dialyzed FCS. At various time points, aliquots of each culture are washed and resuspended in PBS at a determined cell density. This mixture is then sonicated and centrifuged at high speed. From each supernatant, an aliquot is desalted by size-exclusion gel filtration, and subsequently incubated at 30° C. with 5,10-CH$_2$-H$_4$PteGlu and [$^3$H]-FdUMP. An ice-cold suspension of dextran T-70- and BSA-treated charcoal is added, mixed, and then centrifuged about 5 min. The radio-

TABLE 7

Hematological Analyses of CD-1 Mice at Weekly Intervals Receiving po 1-mer at 10 mg/kg Dose Level.

| PARAMETER | REFER | WEEK 1 | WEEK 2 | WEEK 3 | WEEK 4 | WEEK 6 |
|---|---|---|---|---|---|---|
| WBC | 6.9-9.1 thds/cmm | 4.86 | 3.16 | 2.8 | 1.83 | 3.03 |
| MCV | 69-85 fl | 51.5 | 51 | 56 | 52.83 | 51.18 |
| MCH | 24-30 pg | 17.2 | 15.6 | 16.56 | 16.42 | 16.1 |
| SGOT | 24-472 u/l | 335.5 | 911.33 | 1174 | 1549.5 | 1211.61 |
| SGPT | 28-190 u/l | 46.5 | 110 | 177 | 125.66 | 137.55 |
| Potassium | 4.7-6.3 meq/l | 11.63 | 11.1 | 8.9 | 12.46 | 10.82 |
| BUN | 23-43 mg/dl | 24.66 | 18 | 22 | 21.33 | 22.44 |
| Calcium | 12-12.4 mg/dl | 7.56 | 7.75 | 8.85 | 6.5 | 7.7 |
| Sodium | 144-150 meq/l | 155.6 | 142.5 | 152.5 | 161.6 | 162.22 |
| Chloride | 104-120 meq/l | 106.33 | 95 | 87.5 | 86.66 | 89.72 |

TABLE 8

Hematological Analyses of CD-1 Mice at Weekly Intervals Receiving po 1-mer at 15 mg/kg Dose Level.

| PARAMETER | REFER | WEEK 1 | WEEK 2 | WEEK 3 | WEEK 4 |
|---|---|---|---|---|---|
| WBC | 6.9-9.1 thds/cmm | 2 | * | 2.1 | 1.85 |
| MCV | 69-85 fl | 50 | | 56.556 | 51 |
| MCH | 24-30 pg | 16.83 | | 16.56 | 14.2 |
| SGOT | 24-472 u/l | 730 | | 1194 | 1669.5 |
| SGPT | 28-190 u/l | 67.5 | | 120.3 | 123.66 |
| Potassium | 4.7-6.3 meq/l | 8.9 | | 8.7 | 13.46 |
| BUN | 23-43 mg/dl | 26 | | 22 | 20.33 |
| Calcium | 12-12.4 mg/dl | 9.15 | | 7.73 | 6.7 |
| Sodium | 144-150 meq/l | 154.5 | | 156.5 | 165.6 |
| Chloride | 104-120 meq/l | 101.33 | | 87.5 | 81.66 |

Example 15

This example describes measurements of thymidylate synthetase activity, intracellular nucleotide and co-factor concentrations, and growth inhibition.

Measurement of Cellular TS Levels and Activity

To further evaluate the effectiveness of the delivered conjugate, accurate and sensitive methods are used to measure TS levels and activities. The procedures used are adapted from those previously described by Spears et al. ((1988), in *The Expanding Role of Folates and Fluoropyridmidines in Cancer Chemotherapy*, Plenum Publishing, active supernatant is added to a dilute solution of trichloroacetic acid, incubated and centrifuged. The resulting pellets are subsequently dissolved in scintillation fluid for radioactive quantification.

TS Activity

TS activity is measured according to the tritium-release assay described by Spears et al. (supra). The assay consists of incubating a portion of the cytosol with [$^3$H]-dUMP and 5,10-methylene tetrahydrofolate at typically ~0.5-1 µm final concentration at pH 7.3. After the elapsed incubation at 37° C., the reaction is stopped by cooling it to 0° C. The excess [$^3$H]-dUMP is removed by typically adding activated charcoal containing dilute trichloroacetic acid. Following centrifugation, the tritiated water ($3H_2O$) formed during the incubation is measured. Results are expressed as femtomoles of $3H_2O$ formed per minute per milligram protein, based on the linear regression obtained from incubation times. The sensitivity of this method is 10 fmol/min/mg protein.

Nucleotide Concentrations

Equally crucial for the judgment of conjugate effectiveness is the precise determination of the intracellular levels of free and bound nucleotides. These levels are measured before and after each conjugate addition. The rationale for these measurements centers primarily around those studies which have determined that free pools of these nucleosides govern cell growth and regulate TS activity (Berger, supra; Evans et al., (1980), *Cancer Res.*, 40:4113-4122; Evans et al., (1981), *Cancer Res.*, 41:3288-3295). The inter-relationship of excess levels of intracellular FdUMP and dUMP are of a competitive nature. Clearly, at elevated levels of endogenous dUMP, the effectiveness of FdUMP will be reduced. Further, due to the increase in FdUMP binding gained in the presence of LV, the correlation of LV concentration with effectiveness could be gained. Therefore accurate measurement of each concentration enables the assessment of the effectiveness of a given conjugate. To gain this information, analyses are performed to determine the intracellular levels of dUMP, 5FdUMP, and leucovorin.

Measurement of dUMP

This assay is adapted from Moran (*Proc. Natl. Acad. Sci.*, 1979, 76:1456-1460). In this assay, pure thymidylate synthetase (*L. casei*) is used to convert quantitatively a sample of dUMP to [methyl-$^{14}$C]-dTMP that has been incubated in the presence of $^{14}$C-labeled 5, 10-$^{14}CH_2$-$H_4$PteGlu. This process involves treating the TS enzyme with buffered BSA and the unknown amount of dUMP from cell extracts. $^{14}$C-labeled leucovorin (Amersham Life Sciences) is added and the resultant mixture incubated. The methyl-transfer reaction is quenched with formaldehyde and the labeled TMP is isolated using a DEAE-cellulose column and eluted with buffered ammonium bicarbonate or formate. The radioactivity of the eluate is measured by scintillation counting. Sensitivity levels as little as 10 pmoles of dUMP can be reliably obtained.

Measurement of Free and Bound 5FdUMP

In addition to free 5FdUMP concentrations, it is also important to know the amount of [$^3$H]-5FdUMP that is already bound to TS, as this ratio will directly relate to the effectiveness of the intracellular 5FU delivery. This measurement will only apply to those cellular uptake experiments employing tritium-labeled substrates. In general, this method (Moran, supra) involves the addition of BSA- and dextran-treated charcoal to the unknown mixture of free and bound FdUMP. Simple centrifugation with extraction of the supernatant is sufficient to remove unbound, labeled FdUMP with 90-99% efficiency. The ratio of free to bound FdUMP can be obtained by dividing scintillation counting measurements of the supernatant and charcoal layers. This data, when compared to the intracellular levels of dUMP, can provide insight into how well the cell lines resist the adverse effect of 5FU.

Measurement of Leucovorin (LV)

An assay is adapted from the method described by Lu et al. (supra). For these cellular uptake experiments, the hepatic cells will be plated to a pre-determined density in 2 cm$^2$ wells in folate-free medium containing 10% dialyzed horse serum at 37° C. for 24 hrs. The medium will then be aspirated and the cells suspended in medium containing (6S)-[$^3$H]-leucovorin, and incubated at 37° C. After the incubation period, cellular uptake will be stopped by cooling the cells to 0° C. and quickly washing with cold PBS (pH 7.4). To remove cell-surface bound LV, the cells will be further rinsed with cold saline (pH 3.0). After an additional PBS wash, the cells will be solublized and assayed for tritium-containing materials. Non-specifc binding will be subtracted from the final absorbed amount.

Example 16

This example illustrates the bioefficacy of conjugates of the present invention, in particular, po 1-mer, targeted against human hepatoma xenografts in nude mice.

Xenotransplanted tumors have been previously shown to be responsive to 5FU chemotherapy as assayed by direct physical measurement of the tumor (Houghton et al., *Biochem. Pharmacol.*, 36, 1285-1289 (1987)), histological changes and biochemical measurements, such as alpha-fetoprotein (AFP) levels (Lemoine et al., *Pathol. Biol.* (*Paris*), 47, 903-910 (1999)) and thymidylate synthase levels (Peters et al., *J. Clin Oncol.*, 12, 2035-2042 (1994)). The xenograft tumors in nude mice are a widely used model for tumor studies that allows for direct measurement of the growth of human tumors. Male CD-1 nude mice (6-8 weeks old, 20-22 g in weight) were used for these bioefficacy studies. An injection of $10^8$ Hep G2 cells was made subcutaneously into the subcapsular region of each mouse. Mice were observed daily for tumor formation. After tumors emerged, they were measured twice a week in two dimensions with sliding calipers. When the tumors reached a weight of 100 mg in weight as determined by the formula: [(weight, mg)=(length (mm)×width (mm))$^2$/2], treatment was initiated (Geran et al., *Cancer Chemother. Rep.*, 3, 51-61 (1972)). Initially, mice were treated with 10 mg/kg dose once/week for 8 weeks. Subsequently, separate cohorts of mice were treated with 15 mg/kg weekly for 8 weeks and finally 10 mg/kg twice weekly for 8 weeks. The impact of treatment upon tumor growth was judged by direct measurement as described above. In addition, tumor progression was tracked by serological measurements, such as AFP levels. AFP levels were assayed weekly following each injection. Blood was taken retro-orbitally from each mouse. AFP levels were assayed immunochemically, using kits supplied by Abbott Laboratories (Waukegan, Ill.) and based on the methods of Wang et al. (*Cancer Res.*, 50, 869s-872s (1990)). Measurements of AFP levels were intended to complement direct physical measurement as an indicator of tumor progression. Generally, serum AFP levels behave as if they reflect tumor mass. However, it should be noted that moderately raised AFP levels have been found in some patients with uncomplicated liver disease. Despite these false positives, serum AFP levels have been successfully used to monitor response to therapy (Johnson, *J. Gastroent Hepatol.*, 14 (Suppl.), s32-s36 (1999)) especially in the tumor-bearing nude mice, where the human tumor is the only source of human AFP. Results from such assays provide an early indication of HCC potential before it is manifested as physical tumor growth. The data generated by the above experiments should aid in the derivation of starting doses for larger mammal testing and subsequent clinical studies.

po 1-mer at Weekly 10 mg/Kg Dose Level

The treatment of hepatoma-bearing mice with 10 mg/kg po 1-mer induced a mild inhibition of tumor growth. Initial effects of po 1-mer treatment were noticed after about 5 weeks. Overall, however, tumors continued to grow after this point, but at a slower rate than the control. For instance, at 8 weeks post po 1-mer treatment, the average tumor weight of xenografted human hepatomas in nude CD-1 mice was about 7 g, whereas the average tumor weight of the saline control was about 15 g. Histological analysis was performed after 8 weeks in order to compare the tumors of the control cohort with the tumors of po 1-mer-treated nude mice. These analyses revealed a reduced mitotic index and increased amount of necrotic tissue in the treated tumors. Furthermore, a decreased TS activity was noted in the treated tumors, but not in the liver taken from the same animal (Table 9). In general, the weights of the po 1-mer treated mice and the saline control cohort displayed a mild drop off after 3 weeks of treatment in comparison to non-tumor-bearing mice. This weight loss may then be due to the tumor burden, rather than the therapeutic treatment, and was continued through week 8.

TABLE 9

Effects of po 1-mer on the Inhibition of TS Activity in the Liver and Tumor of Xenografted Human Hepatomas in Nude CD-1 Mice at Weekly 10 mg/kg Dose Level.

| TISSUE | COUNTS/MG PROTEIN | % TS INHIBITION |
| --- | --- | --- |
| Tumor | | |
| Treated | 17641 | 50 |
| Untreated | 35197 | — |
| Liver | | |
| Treated | 19718 | 3.84 |
| Untreated | 20504 | — | po 1-mer at Weekly 15 mg/Kg Dose Level

When po 1-mer dose level was increased to weekly injections of 15 mg/kg, a more dramatic effect in tumor weight was elicited. At this dose level, po 1-mer treatments had a greater impact on tumor progression, inducing a significant decrease in growth rate after 5 injections. At this point, tumor progression was almost static. After 2 additional injections, the tumor burden was eradicated in one mouse and the tumor size was reduced in the others. As the size of these tumors was reduced, the tissue appeared dried and necrotic. This was in stark contrast to the saline-treated control, wherein the tumor weight increased to about 12 grams over a four week period. A decline in alphaferotin protein (AFP) measurements roughly paralleled the reduction of tumor size. PO 1-mer treatment dramatically reduced AFP levels such that, after 3 weeks of treatment, the level of AFP was less than 200 μg/ml. This trend continued until the values were below the level of detection at week 8.

After the treatment was completed, tumors were analyzed both histologically and for TS activity. These analyses revealed greatly reduced TS activities in the treated tumor, but not liver tissue from the same animal (Table 10). Histologically, the po 1-mer treated tumor displayed a very low mitotic index and extensive necrosis. In terms of clinical toxicity, the po 1-mer treated mice maintained a steady weight gain equivalent to that of a non-tumor bearing mice. The nude mice of this bio-efficacy study that were sacrificed during the course of the experiment displayed approximately the same blood chemistry profile as those normal mice in the toxicity experiments. Therefore, it can be deduced that increasing the dose of po 1-mer increased the efficacy without increasing systemic toxicity.

TABLE 10

Effects of po 1-mer on the Inhibition of TS Activity in the Liver and Tumor of Xenografted Human Hepatomas in Nude CD-1 Mice at Weekly 15 mg/kg Dose Level.

| TISSUE | COUNTS/MG PROTEIN | % TS INHIBITION |
| --- | --- | --- |
| Tumor | | |
| Treated | 8591 | 75.6 |
| Untreated | 35197 | — |
| Liver | | |
| Treated | 18989 | 7.39 |
| Untreated | 20504 | — | po 1-mer at 10 mg/Kg Dose Level Twice-Weekly

Further investigation of po 1-mer efficacy against HCC tumors was extended to consider alterations in schedule as well as dose. In this alteration, tumor-bearing mice were treated with 10 mg/kg twice weekly with po 1-mer or saline control. On this schedule, po 1-mer therapy affected changes in tumor growth more quickly. A significant reduction in tumor progression was observed after 3 weeks of treatment with a moderate reduction in body weight. This reduction in tumor growth then continued with regular twice-weekly treatments until the tumors were beyond detection after 6 weeks. Again, AFP measurements of po 1-mer-treated mice roughly paralleled the rate of tumor reduction beginning with week-3 and continuing until they were below the limits of detection at week 6. In contrast, the AFP levels of saline-treated mice rose from 50 μg/ml to 900 μg/ml over the 7 week period. One animal in this cohort did display some resistance to treatment, with tumor growth continuing through week 5. However, when this animal was sacrificed due to a viral infection, histological analysis revealed extensive necrosis of the tumor in comparison with the saline control.

Example 17

This example illustrates the synthesis of 5FdU 18-mer with and without the C6-thiol modifier (FIG. 11).

All oligonucleotides were synthesized on an Applied Biosystems 392 DNA synthesizer, using standard methylphosphonate/phosphoramidite chemistry. The solid phase DNA syntheses used Glen research chemicals (Universal-Q solid support (500 Å pore size), phosphoramidite activator solution (1H-tetrazole), and β-cyanoethylphosphoramidites), or self-prepared chemicals (deblock solution, cap A solution, cap B solution, and oxidizer solution). The deblock solution contained 2.5% (v/v) dichloroacetic acid in methylene chloride (reagent grade). Cap A was a mixture of acetic anhydride in dry tetrahydrofuran and doubly distilled 2,6-lutidine (1:8:1; v/v/v). Cap B was a 0.5 M solution of 1-methylimidazole in anhydrous $CH_3CN$. For the sulfurization of trivalent phosphites, a solution containing 3H-1,2-benzodithiole-3-one-1,1-dioxide (Beaucage's Reagent) at a concentration of 100 mg reagent in 10 ml $CH_3CN$ (Glen Research) was used.

Two user programs were developed for the synthesis of this oligonucleotide. The first program, entitled "DBL SULFUR" was invoked to synthesize the phosphorothioate linkages. This program passed twice the normal amount of synthon through the column at an increased coupling time (i.e., from 25 seconds to 60 seconds). The oxidation/sulfurization time was set at 900 seconds.

Polyacrylamide gels were prepared by dilution of a 30% aqueous solution (by weight) of 14:1 acrylamide: N,N'-methylene-bis(acryl)amide to provide a 15% or 20% crosslinked gel, as indicated in the specific procedure. The final solution contained urea (7 M final concentration). An aliquot of 110 µl of a 20% aqueous solution of ammonium persulfate was added and polymerization was initiated by the addition of tetramethylethylenediamine (TMEDA) (55 µl). The gel was allowed to polymerize and set for 1 hr. The reservoirs were filled with TBE buffer. The sample (8.0-12.0 µl) was added to the gel well. The gel was run under the conditions specified for individual experiments. The radiolabeled product bands were then visualized by autoradiography.

The synthesis of the 5-fluoro-2'-deoxyuridine-containing oligonucleotide was accomplished using existing automated DNA synthesis techniques and methodologies (FIG. 11). The synthesis was carried on a 1 µmole scale using the Universal-Q CPG solid support. As described above, the 5FU oligonucleotide synthon, 5'-dimethoxytrityl-5-fluoro-2'-deoxyuridine, 3'-[(2-cyanoethyl)-(N,N-diisopropyl)] phosphoramidite (Glen Research) was used at 0.1 M (0.25 g in 3.4 ml $CH_3CN$) concentration. The dimethoxytrityl cation absorbances ($\lambda_{max}$ 498 nm) were monitored and measured for coupling efficiency. Upon completion of the last synthetic cycle, the solid-support bound oligonucleotide was removed from the synthesizer and dried in vacuo, prior to deprotection. Alternatively, the solid-support bound oligonucleotide was then exposed to the standard phosphoramidite conditions using the thiol-modifier C6 S-S reagent, 1-O-dimethoxytrityl-hexyldisulfide, 1'-[(2-cyanoethyl)-(N, N-diisopropyl)]-phosphoramidite (0.1 M). To aid in purification, the final dimethoxytrityl (DMT) was allowed to remain intact.

In both cases, with and without the thiol-modifier, the solid-support bound oligonucleotide was treated with 1 ml of a 0.5 M solution of NaOH in 50% $CH_3OH/H_2O$ for 1 hr at room temperature (25° C.). The solution was then neutralized with 2 ml of 0.5 M $Na_2PO_4$ and diluted to 20 ml with $H_2O$. The crude solution was then applied to a pre-equilibrated C18 SepPak (20 ml) for purification. The column was pre-equilibrated with successive elutions with $CH_3OH$ (30 ml), 50% $CH_3OH/H_2O$ (30 ml), then $H_2O$ (100 ml). After application of the crude oligomer, the column was washed with $H_2O$ (30 ml) and then 5% $CH_3CN/H_2O$ to remove any failure sequences from the synthesis. The column was then returned to $H_2O$ (30 ml) and treated with 0.5% (v/v) $CF_3CO_2H$ in $H_2O$. The acid excesses were then washed from the column using $H_2O$ (30 ml). The oligomeric product was eluted from the column using 35% $CH_3CN/H_2O$ and fractions were collected. The fractions containing the product as identified by HPLC and PAGE analyses were pooled and concentrated to yield 78 O.D. for un-thiol-modified oligonucleotide, and 37 O.D. for the thiol-modified oligonucleotide. Yields were determined spectrophotometrically.

Example 18

Figure 10:
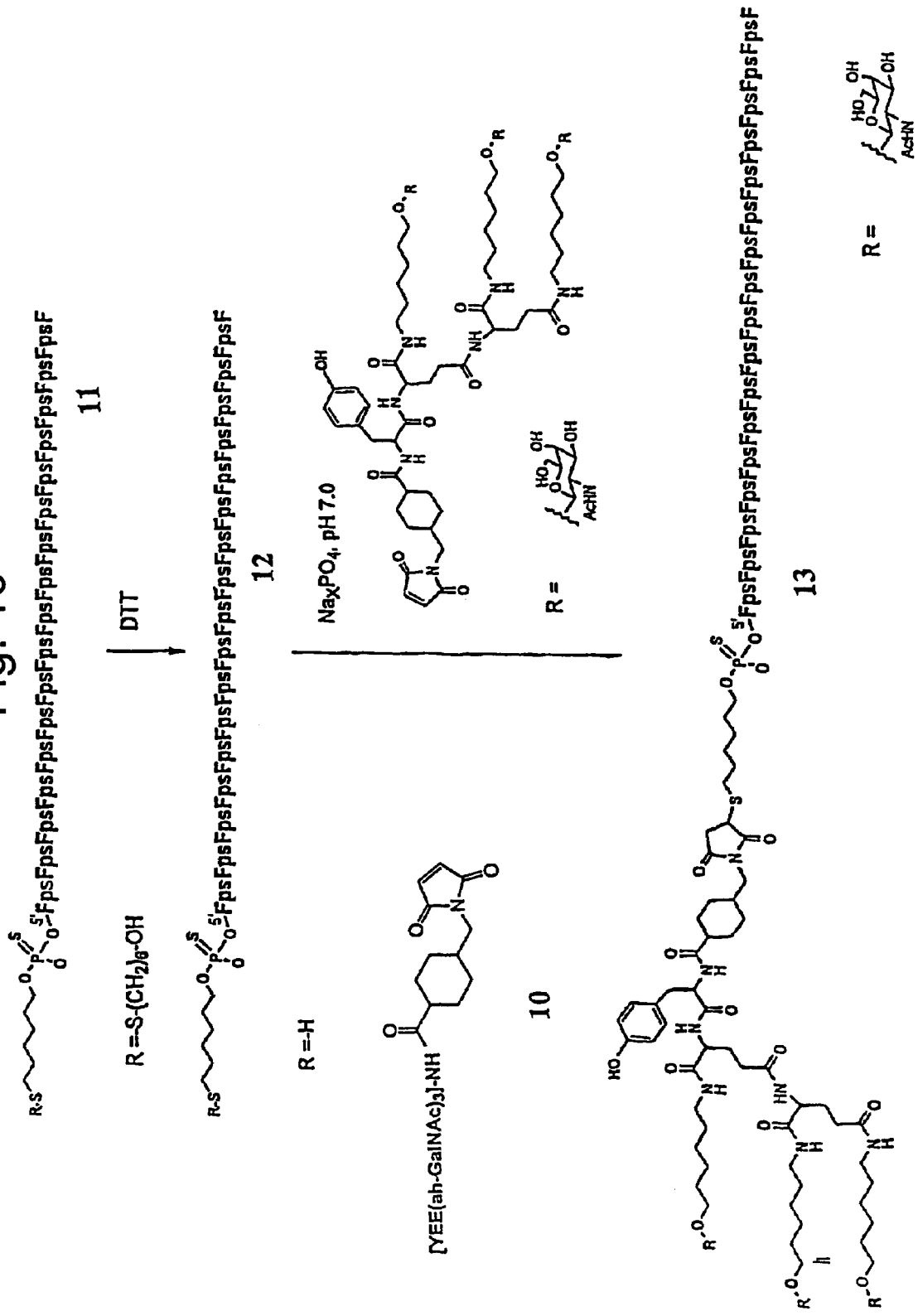
FIG. 10 shows a detailed reaction scheme for the preparation of 5-fluoro-2'-deoxyuridine conjugates (18-mer).

This example illustrates the preparation of the thiol-modified oligonucleotide (12, FIG. 10).

Reduction to thiol (12, FIG. 10) was effected by the treatment of the 5'-disulfide-containing oligomers with DTT. Thus, a 3.6 $OD_{260}$ (~40 nmoles) disulfide oligomer (11, FIG. 10) was dissolved in 400 µl of freshly prepared and degassed 50 mM DTT solution in 10 mM sodium phosphate, pH 8. The mixture was incubated at 37° C. for 2 hrs. The thiol oligomer was then purified on a Sephadex G-25 (fine) column (1.0×43 cm) to remove DTT and inorganic salts. Column packing and sample elution were effected by the use of degassed 20% ethanolic $H_2O$. The G-25 fraction containing the pure thiol oligomer was used immediately in the next reaction to minimize possible thiol dimerization products.

Example 19

Figure 12:
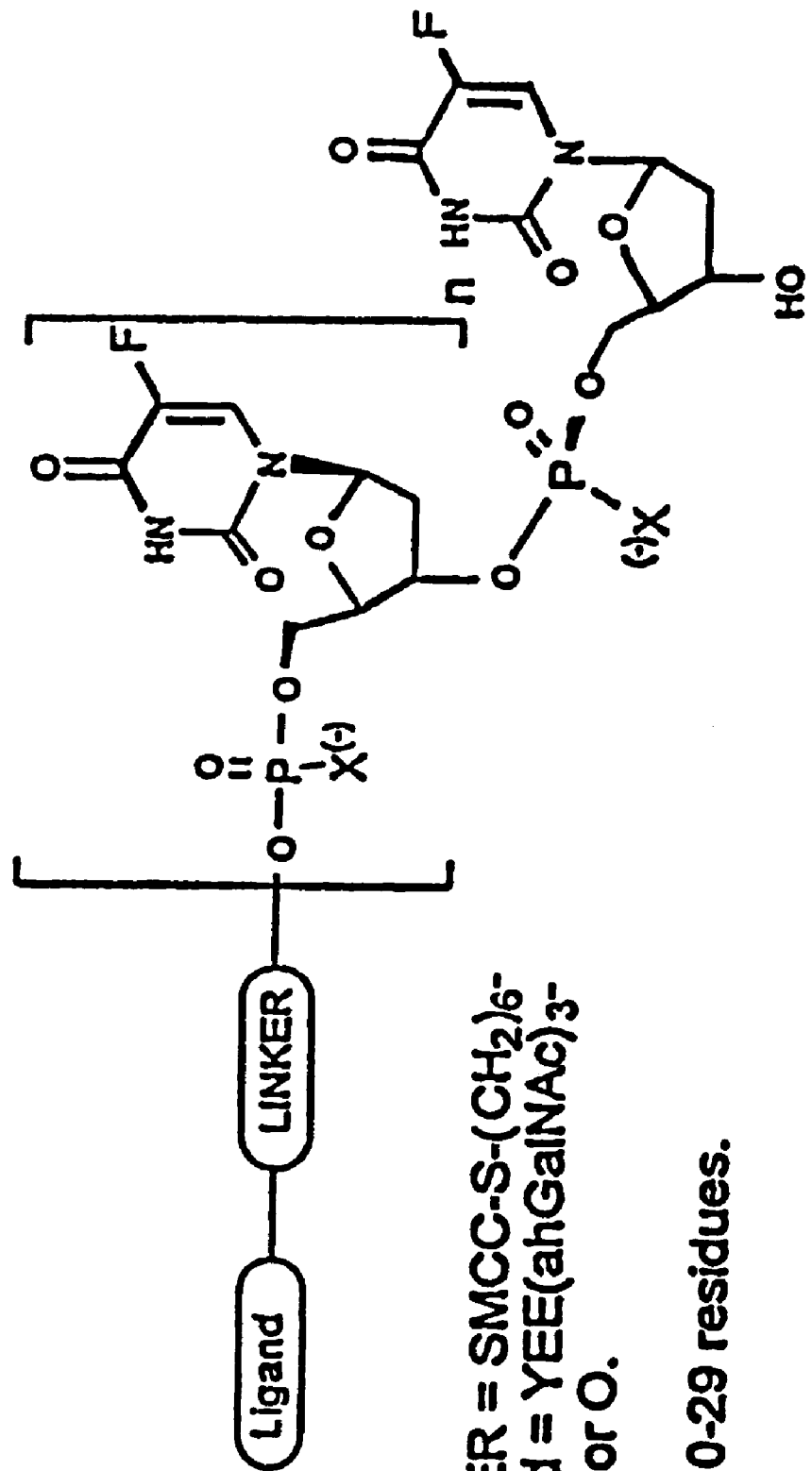
FIG. 12 depicts structures of fluorodeoxyuridine conjugates (18-mer).

This example illustrates the conjugation of thiol-containing oligomer with SMCC-ligand: $YEE(ahGalNAc)_3$-SMCC-AHT-Poly5FU Conjugate (FIGS. 10 & 12) (13).

The G-25 fraction containing 3.6 $OD_{260}$ (40 nmoles) pure thiol oligomer (12, FIG. 10) was mixed with SMCC-YEE(ahGalNAc)$_3$ (10, FIG. 10) ("A-L" conjugate) (100 nmoles) immediately after it was collected and the mixture was concentrated to dryness in vacuo using a Speed-vac. The residue was dissolved in 100 µl of degassed 50% $CH_3CN$ containing 0.1 M sodium phosphate, pH 7. The solution was further degassed in a Speed-vac by applying vacuum for about 5 min. The solution was then capped tightlt and incubated at room temperature overnight to allow conjugation to go to completion. Yield was measured by intensity of $A_{267}$ absorbance (1 nmole is 0.089 O.D.), then analyzed by 20% denaturing PAGE with ultraviolet shadowing. This result indicated quantitative conjugation of the thiol oligomer with the neoglycopeptide. The conjugate (FIG. 13) was confirmed by its significant gel mobility shift upon chymotrypsin digestion and its inability to shift upon DTT treatment. The conjugate was finally purified by a Sephadex G-25 column by eluting with 20% ethanol, and then used in further studies. Yield 32.4 nmoles (3.85 $OD_{260}$); mass spectrum (MALDI-TOF), m/z 6712 ($C_{241}H_{291}N_{46}O_{63}P_{18}S_5F_{18}$ requires 6712 (M)$^+$ (Scripps Research Institute, La Jolla, Calif.)).

Example 20

Figure 2:
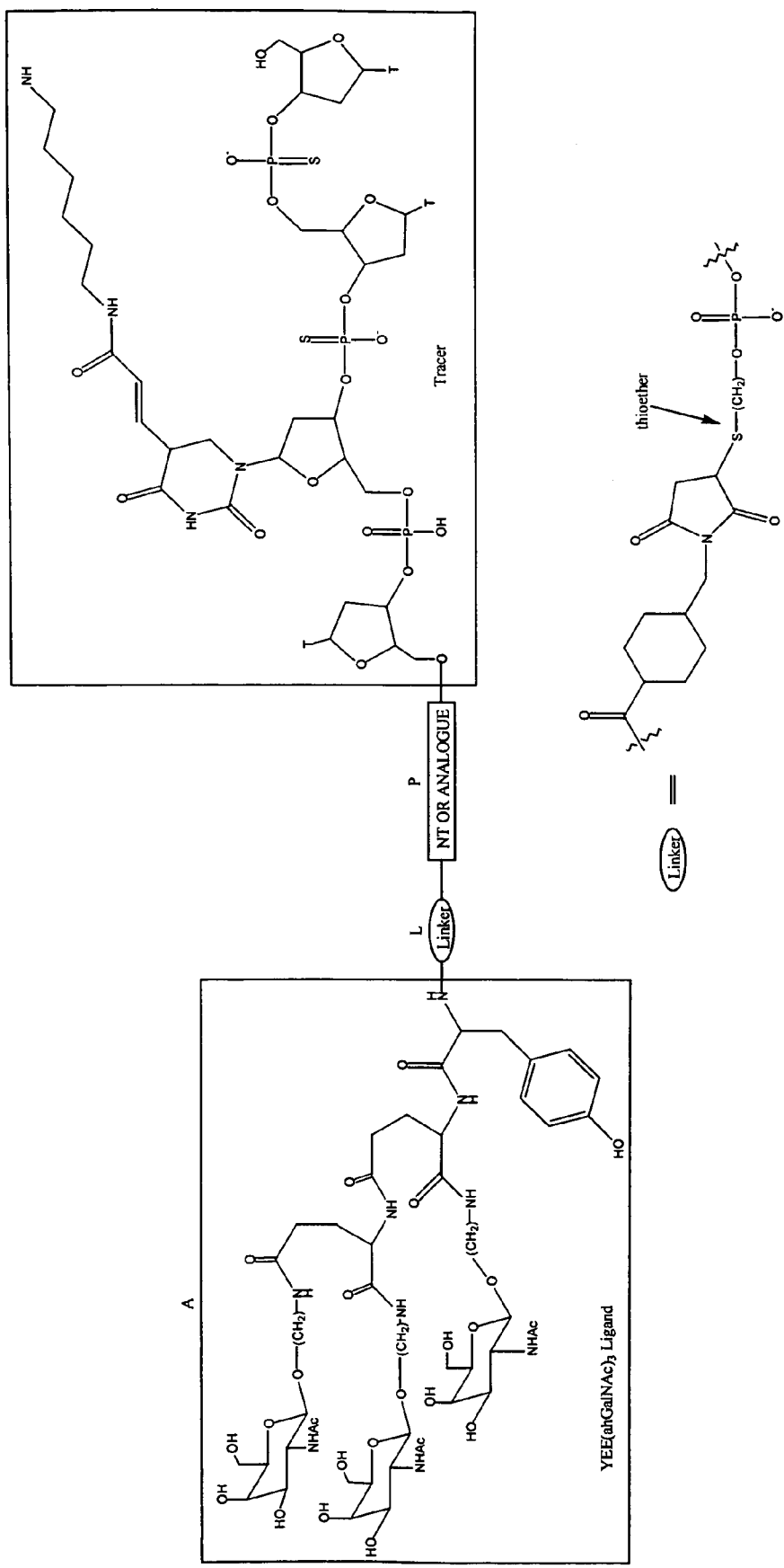
FIG. 2 depicts a molecular assembly of ligand-specific A-L-P conjugate with a tracer.

This example illustrates the installation of $^{35}S$ radiolabel tracer (FIG. 2).

Reactions mixtures (300 µl total volume) consisted of 18.1 nmoles 5FU oligonucleotide substrate (18-mer), 5× terminal deoxynucleotidyl transferase buffer (pH 7.2) (60 µl), 0.5 mCi of [$^{35}S$] dATP S (Amersham, Uppsala, Sweden), and 500 units of terminal deoxynucleotidyl transferase (Life Technology, La Jolla, Calif.). The resulting solution was incubated at 37° C. for 17 hrs. The mixture was then cooled to room temperature and diluted with 400 µl of 0.5 M $Na_2PO_4$ (pH 5.8), and then after 1 hr, the contents were applied to a pre-equilibrated NAP-25 column (Pharmacia, Peapack, N.J.). After the 700 µl of the sample were loaded, 300 µl of $H_2O$ were loaded, and the entire 1 ml aliquot was collected as fraction 1. Subsequently, fractions of 1 ml were collected; fraction 4 contained the product that was quantified by UV and scintillation counting. From these measurements the specific activity (µCi/nmole) was calculated. The yield was 10.42 nmoles containing a total of 183.3 µCi.

Example 21

This example illustrates the methods and materials utilized for cellular uptake experiments using the A-L-PP conjugates, wherein PP is a pharmaceutical agent containing anti-cancer activity and further illustrates the enhanced and specific cellular uptake of the neoglycoconjugate by Hep G2 cells in vitro.

Hep G2, TSU and Caki-1 cells (ATCC, Rockville, Md.) were passaged into 2 cm$^2$ wells and grown in RPMI medium 1640 supplemented with L-glutamine and FCS to a density of $0.2 \times 10^6$ to $0.5 \times 10^6$ cells per well.

The maintenance medium was aspirated and the cells were incubated at 37° C. with 0.2 ml medium that contained 2% FCS and was made 1 µM in [5'-$^{32}$P]-labeled conjugate or the corresponding unconjugated oligomer. After the prescribed time had elapsed, a 5 µl aliquot of the medium was saved for scintillation counting and the remainder was aspirated from the well. The cells were washed with D-PBS (2×0.5 ml), treated with 0.25% trypsin (0.25%; prepared in HBSS with 1.0 mM EDTA) (GIBCO BRL, Carlsbad, Calif.) at 37° C. for 2 min, and suspended in fresh growth medium containing 10% FCS. The suspended cells were layered over silicon oil (0.5 ml) in a 1.7 ml conical microcentrifuge tube and pelleted by centrifugation at 14,000 rpm (12,000 g) for 30 seconds. The supernatant was carefully decanted and the cell pellet was lysed with 100 µl of a solution containing 0.5% NP 40, 1 00 mM sodium chloride, 14 mM Tris/HCl and 30% acetonitrile. The amount of radioactivity, and by inference the amount of neoglycoconjugate or oligomer associated with the cell lysate, was determined by scintillation counting.

The cellular association of the phosphorothioate-linked, 5 FU-containing neoglycoconjugate with Hep G2 cells was examined in order to demonstrate enhanced uptake in cells of hepatic origin. As a control, cellular association of the corresponding unconjugated oligomer labeled with Hep G2 cells was also examined: The neoglycoconjugate rapidly associated with Hep G2 cells to the extent of 19.54 pmoles/$10^6$ cells at 0.5 hrs and continued accumulating until a peak value of 39.91 pmoles/$10^6$ cells was reached at 4 hrs. In contrast, the corresponding unconjugated oligomer displayed a lower rate of cellular uptake by Hep G2 cells, associating to the extent of 6.51 pmoles/$10^6$ at 0.5 hrs, and further accumulating to a peak value of 11.88 pmoles/$10^6$ at 4 hrs. Cell specificity of the compounds was also examined. The asialoglycoprotein receptor is found on the surface of hepatocytes and is an efficient means for selectively targeting this tissue for a variety of therapeutic agents. Tissue specificity was examined by assaying the association of neoglycoconjugate with two human cell lines of non-hepatic origin, TSU and Caki-1.

Incubation of TSU cells with the unconjugated oligomer resulted in an initial uptake of 3.8 at 0.5 hrs, which gradually increased to a value of 11.43 at 4 hrs. These results are similar to those observed when the unconjugated oligomer was incubated with Hep G2 cells. However, when TSU cells were exposed to the neoglycoconjugate, no significant increase in uptake was apparent. The neoglycoconjugate was taken up to the extent of 5.6 at 4 hrs and gradually accumulated to a value of 13.15 at 4 hrs, values very similar to those seen with the unconjugated oligomer.

In a similar fashion Caki-1 cells did not display increased uptake of the neoglycoconjugate. In comparison to the unconjugated oligomer, the neoglycoconjugate accumulated to the extent of 6.4 at 0.5 hrs and 10.553 at 4 hrs. Similar data were observed with the unconjugated oligomer, which displayed association of 7.66 at 0.5 hrs and 11.86 at 4 hrs. Both of the neoglycoconjugate and the corresponding unconjugated oligomer were proven to be structurally stable in cell culture media for up to 96 hrs.

The above data demonstrate that the neoglycoconjugate is capable of delivering a chemotherapeutic agent, namely 5FU, to hepatocytes in an enhanced and specific manner to cells of hepatic origin.

Example 22

This describes the enzymatic degradation of the 5-FU oligonucleotide and corresponding conjugate in vitro and intracellularly in Hep G2 cells.

The phosphorothioate oligonucleotide (18 residues of 5-fluoro-2'-deoxyuridine 5FdU) units linked by phosphorothioate moieties) was first degraded to smaller oligonucleotides (approximately 5 oligomers, based upon HPLC analyses as described below), and then to monomeric units over the time course of exposure to enzyme or Hep G2 cells. While complete conversion to monomeric units was observed with the Hep G2-internalized oligonucleotide (100% production of monomeric 5FdUMP residues), the enzymatic treatment of the oligonucleotide produced a maximum of only 72% of the calculated amount of 5FdUMP after 144 hrs. However, despite this, it is important to point out that the enzymatic digestions performed with S1 nuclease do not represent the best model for this example, but only represented a guideline from which to use the more realistic cellular model. Further, although complete degradation to monomeric units by the endonuclease S1 nuclease was not observed, there was complete degradation of the oligonucleotide into the smaller fragments after only 24 hrs.

Calculation of Molar Extinction Coefficient of5FdUMP

A sample of 5FdUMP (5 mg (0.015 mmole)) was dissolved in 5 ml of $H_2O$. This solution was then diluted to give solutions: 1.9 µM, 3.8 µM, 9.5 µM, 19 µM, 38 µM, and 95 µM. A Beer's law plot was prepared and the extinction coefficient was calculated to be 5278 $cm^{-1}L^{-1}M^{-1}$; $r^2=1.0$. Based upon this value, an extinction coefficient was calculated for the 5FU oligonucleotide (ps5FU-18-mer). This value was 1 nmole at 0.089 O.D. (260 nm).

Preparation of the HPLC Standardization Curve for 5-fluoro-2'-deoxyuridine 5'-Monophosphate Standard solutions containing 5-fluoro-2'-deoxyuridine 5'-monophosphate (Sigma-Aldrich, St. Louis, Mo.) were prepared: 0.38 µM, 0.95 µM, 3.8 µM, 7.6 µM, 38 µM, and 95 µM. These concentrations were determined by UV spectroscopy. A Microsorb Rainin column (5 µM) (4.6 mm×150 mm) was used; standardization was achieved by measuring the HPLC peak areas of the solutions with known concentrations (100 µl sample, 100 µl injector loop). Samples containing 5FdUMP in each standardized solution were run using 50 mM $Na_2PO_4$ (pH 5.8) in 2% $CH_3CN/H_2O$ at a flow rate of 1.0 ml/min. The oligomeric products were eluted using a linear gradient of $CH_3CN$ (2% to 50% $CH_3CN$ in 20 min) in 50 mM $Na_2PO_4$ (pH 5.8). Each concentration and time point was run in triplicate. The eluant was monitored at 267 nm. The elution times and concentrations of the standards were as follows: 5FdUMP: 2.71 minutes; 5FU oligonucleotide: 19.6 min. A correlation was drawn between the area of the peak displayed on the chromatogram and the concentration of 5FdUMP. The equation is:

concentration (µM) of 5FdUMP=[(peak area observed−1575.060)/10158.229].

Degradation ofthe 5FU Oligonucleotide by S1 Nuclease

Reaction mixtures (320 µl total volume) contained 4.32 O.D. (48.5 nmoles) of 5FU oligomer in 30 µl of 10×S1 reaction buffer and diluted with 50 µl of $H_2O$. To this solution, an aliquot of 120-µl of S1 Nuclease (Life Technologies, 263 units/µl) (One unit produces 1 µg of acid soluble nucleotides per minute at 37° C.) was added to initiate the reaction. The reaction mixture was then incubated at 37° C. for the allotted time: 24, 48, 72, and 144 hrs. At each time point, a 10-µl aliquot was withdrawn and analyzed by HPLC using UV spectroscopic detection at 260 nm. A Microsorb Rainin column (5 µm) (4.6 mm×150 mm) was used; standardization was previously achieved by measuring the HPLC peak areas of the solutions with known concentrations (100 µl sample, 100 µl injector loop). Samples containing 5FdUMP in each aliquot were run using 50 mM $Na_2PO_4$ (pH 5.8) in 2% $CH_3CN/H_2O$ at a flow rate of 1.0 ml/min. The oligomeric products were eluted using a linear gradient of $CH_3CN$ (2% to 50% $CH_3CN$ in 20 min) in 50 mM $Na_2PO_4$ (pH 5.8). Five oligomeric species were observed: 15.9, 17.2, 17.5, 18.35, 18.6 min.

Degradation of 5FU Oligonucleotide Conjugate by Hep G2 Cells and Conjugate Treatments Incubation of Hep G2 cells with 1 µM of 5FU oligonucleotide conjugate contained within the media for 24 hrs allowed for sufficient uptake as described by an earlier example. The lysate was then used directly for analysis of oligomer degradation by HPLC. A Microsorb Rainin column (5 µM) (4.6 mm×150 mm) was. used. Standardization was previously achieved by measuring the HPLC peak areas of the solutions with known concentrations (100 µl sample, 100 µl injector loop). Samples containing 5FdUMP in each lysate solution were run using 50 mM $Na_2PO_4$ in 2% $CH_3CN/H_2O$ at a flow rate of 1.0 ml/min. Oligomeric products were eluted using a linear gradient of $CH_3CN$ (2% to 50% $CH_3CN$ in 20 min) in 50 mM $Na_2PO_4$ (pH 5.8). No oligonucleotide fragments were observed from the Hep G2 lysate.

The metabolism of the proposed conjugates is a crucial step to the therapeutic effectiveness of this approach. It has been previously established that the neoglycopeptide ligand is rapidly degraded upon entrance to the cell (Hangeland et al., *Antisense Res. Nucl. Acid Drug Develop.*, 7:141-149 (1997)). Further, the phosphodiester-linked fluorodeoxyuridine string should also be rapidly hydrolyzed, releasing the 5FdUMP residues. At this juncture, it is important to note that oligonucleotide phosphodiesters are unstable living systems and are rapidly degraded (Sands et al., *Mol. Pharmacol.*, 47:636-646 (1995)). However, this degradation is advantageous since 5FdUMP is the actual TS inhibitory agent, not 5FU, thereby circumventing the need for thymidine phosphorylase (Zimmerman et al., *J. Biol. Chem.*, 239:2618-2621 (1964)) and thymidine kinase (Umeda et al., *Cancer Res.*, 28:2539-2538 (1968)). As relating to further degradation of the 5FdUMP, the liver and kidneys represent the primary sites for 5-fluorouracil. These degradation products have been previously investigated (Diasio et al., *Clin. Pharmacokin.*, 16:215-237 (1989)). Determinations of this type are carried out using various analytical procedures, such as paper chromatography and HPLC techniques (Sommadossi et al., *J. Biol. Chem.*, 257:8171-8176 (1982); Sommadossi et al., *Cancer Res.*, 45:116-121 (1985)).

Figure 13:
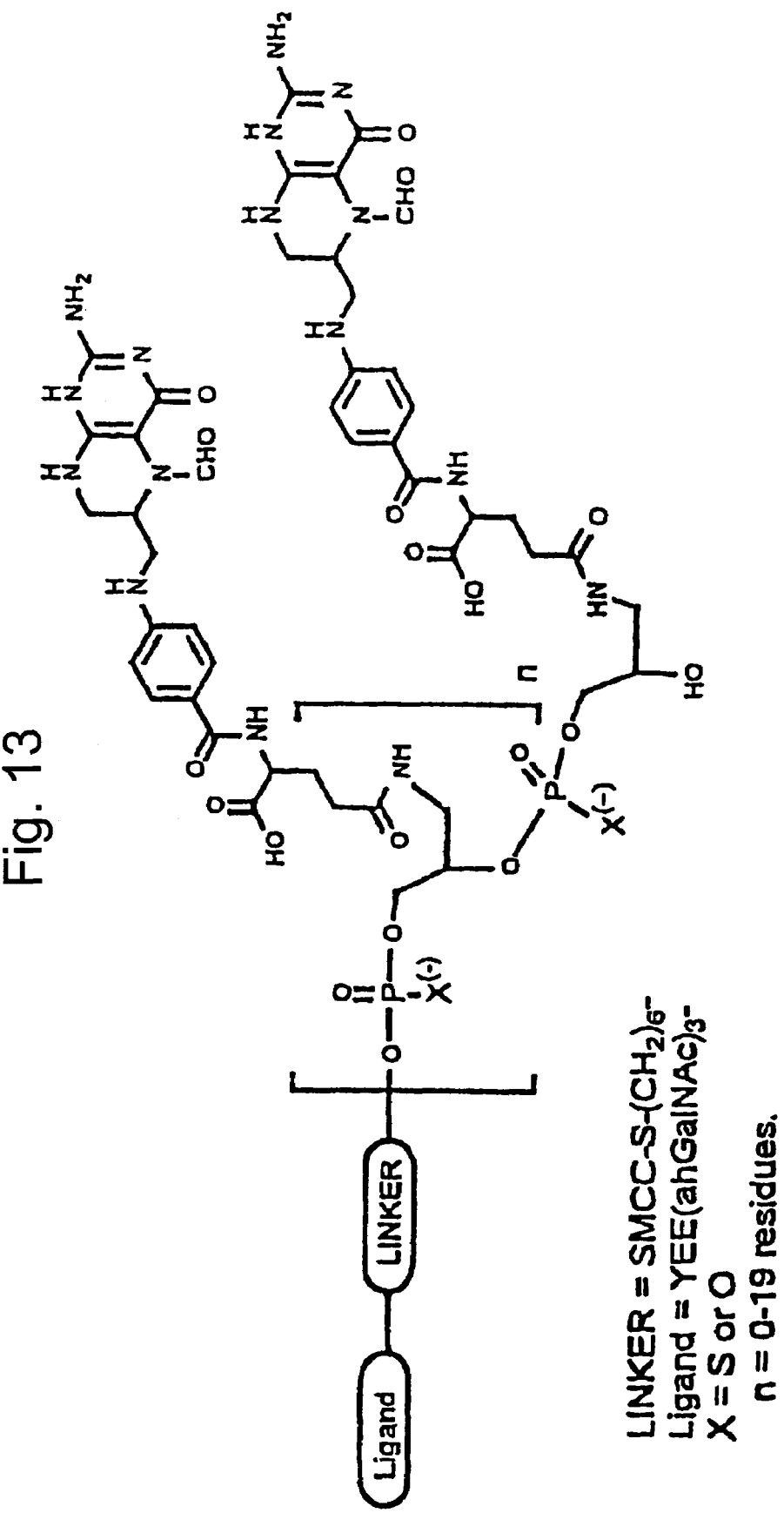
FIG. 13 shows the structures of leucovorin conjugates.

Additionally, to enhance the effectiveness of 5FdUMP binding, a folate co-factor can be administered. To accomplish this on an intracellular level, the ligand-derived leucovorin conjugate is administered. FIG. 13 shows the structure of an A-L-PP multiple leucovorin-containing conjugate. These residues would be liberated upon cleavage of the amide bond linking them to the phosphodiester, non-nucleosidic backbone. The intracellular generation of 5FdUMP and LV by degradation of the conjugates should be beneficial to TS inhibition and detrimental to cell function.

In conclusion, analyses of degradation products can be accomplished by several methods. Most commonly employed is HPLC analysis, using an ion-pair reversed-phase column with porous polymer packing as described (Leyva et al., (1984), *Cancer Res.*, 44:5928-5933; El-Sayed et al., (1983), in *Pharmacokinetics of Anticancer Agents in Humans*, Amsterdam, Elsevier, pp. 209-227). When available, either commercially or readily synthesized, authentic standards are used for comparison.

Example 23

This example illustrates the effect of the phosphorothioate-linked 5FU-containing oligomer and the thioate-linked F50 on cellular proliferation and the specificity of the effect on cells of hepactic origin.

Materials: RPMI supplemented with L-glutamine, D-PBS, and trypsin (0.25%; prepared in HBSS with 1.0 mM EDTA) were purchased from GIBCO BRL. Hep G2, TSU and Caki-1 cells were purchased from ATCC. 48-well cluster plates were purchased from Costar Corp. (Cambridge, Mass.). Cells were counted using a Coulter Cell Counter (Coulter Corporation, Hialeah, Fla.).

Methods: Either Hep G2, TSU or Caki-1 cells were seeded into a 48-well plate in RPMI supplemented with 10% dialysed FCS at a density of $5 \times 10^4$ cells/well. Cells were then allowed to incubate at 37° C., 95% RH, 5% $CO_2$ for 24 hrs. After this incubation period, the maintenance medium was aspirated and cells were treated with 1 µM of either neoglycoconjugate or oligomer in 200 µl of RPMI supplemented with 10% dialysed FCS. Control wells were treated with 200 µl of RPMI+10%DFCS alone. At 0, 24, 48, and 72 hrs, six wells for each condition were washed twice with 0.5 ml of DPBS and treated with 0.5 ml of trypsin (0.25%; prepared in HBSS with 1.0 mM EDTA). Cell numbers for each condition were determined by using a Coulter electronic cell counter.

Hep G2, TSU or Caki-1 cells were treated with a 1 µM of either neoglycoconjugate or oligomer as described in Example 5. The average cell number for six replicate wells was determined for each treatment and an untreated control at 24, 48, and 72 hrs. Treatment of Hep G2 cells with the unconjugated oligomer resulted in a significant decrease of 30-40% in proliferation as compared to the untreated control. Minimal proliferation was observed during the experiment with the cells achieving only 0.5 population doublings over 72 hrs of treatment. In contrast, untreated controls displayed 2.5 pd during the same period. Treatment of Hep G2 cells with the neoglycoconjugate resulted in a decrease in cell number of 55-60% when compared with the untreated control. In addition, cell numbers actually decreased after treatment with the neoglycoconjugate and did not recover to initial control levels during the experimental period, indicating a possible cytotoxic effect of the neoglycoconjugate when used at this concentration.

Specificity of the treatment for cells of hepatic origin was also examined. TSU or Caki-1 cells were treated with a 1 µM concentration of either neoglycoconjugate or oligomer in a similar fashion to Hep G2 cells. In this case, treatment with the unconjugated oligomer resulted in a decrease in cell number of 30-50% when compared to the untreated control. Treatment of these cells with the liver-specific neoglycoconjugate yielded almost identical results to cells treated with the unconjugated oligomer, resulting in no further decrease of cell number. These data confirm the specificity and increased bioefficacy of the neoglycoconjugate in cells of hepatic origin.

Example 24

This example describes assays that can be used to test the efficacy of po 1-mer and ps 1-mer at inhibiting cell cycle progression, viral polymerase activity, and viral cytopathic effects.

Cell-cycle distribution assay

Cells are seeded in 100 mm culture dishes, incubated for 48 hr, and exposed to various concentrations of po 1-mer or ps 1-mer for 24 hr at 37° C. (5% CO2) or for various periods of time (0-48 hr) with a fixed concentration. Afterwards, the cells are incubated with 10 µM BrdUrd for 30 min at 37° C. (5% CO2). The supernatant with dead cells and the harvested living cells are fixed in pre-cooled (−20° C.) ethanol (80%) and stored at −20° C. for up to 3 days. BrdUrd/propidium iodide staining is carried out as described previously (see, e.g., Horber et al., *Br J Cancer*, 72:1067-1073 (1995)). Briefly, after centrifugation, the cells are treated with 2 M HCl for 30 min at 20° C., resuspended in 50 µl PBS, 0.5% Tween-20 and 1% BSA, and incubated with FITC-labeled anti-BrdURd antibody for 30 min at 20° C.; 1 ml PBS/propidium iodide (10 mg/ml) is then added. Stained cells are analyzed with an Epics Elite Analyzer (Coulter, Fla., USA). Singly fluorescent samples (FITC or propidium iodide) are used to optimize instrument settings and ensure proper electronic compensation. See Cattaneo et al., *J. Cancer Res. Clin. Oncol.* 126:247-256 (2000) for more details.

Cytopathic Effect Inhibition Assay

Briefly, cells are treated with po 1-mer or ps 1-mer and infected with a virus. After 6 days, viable cells are counted by using a hemocytometer in conjunction with the trypan blue dye-exclusion method.

Inhibition of Purified HIV-1 RT

Twenty µl assay mixtures contained 50 mM Tris (pH 8.3); 10 mM $MgCl_2$; 50 mM KCl; 5 mM dithiothreitol; 1.0 µM preannealed primed template, 5'$^{32}$P-labeled dGpApTpTpC-pApGpCpTpApGpTpCpCpA) primer and d(CpApApA-pCpTpGpTpGpApTpApCpGpApTpGpG-pApCpTpApGpCpTpGpApApTp C) template; 250 µM each dNTP; and variable concentrations of po 1-mer or ps 1-mer. Reactions are initiated by addition of HIV-1 RT at 10 nM and continued for 15 min at 37° C. Under these conditions, the enzyme was saturated with respect to both substrates. Reaction mixtures are fractionated by denaturing polyacrylamide gel electrophoresis.

Inhibition of Other Viral DNA Polymerases

Experimental analyses are essentially identical to those described for HIV-1 RT (Marshall et al., *Proc. Natl. Acad. Sci.* 89:6265-6269 (1992)). Purified calf thymus α polymerase (Pol α) can be obtained from R. Kuchta (University of Colorado), avian myeloblastosis virus (AMV) RT can be obtained from Life Sciences (St. Petersburg, Fla.) and the Klenow fragment of *E. coli* DNA polymerase (Pol I) can be obtained from U.S. Biochemical. Enzyme concentrations are identical in all cases (10 nM). Primed template is added at concentrations necessary to give polymerizations similar to those observed with HIV-1 RT. 0.05 µM with AMV RT, 5.0 µM with Pol I Klenow fragment, and 2.0 µM with Pol α.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A structurally homogenous conjugate of formula A-L-P wherein
A is;

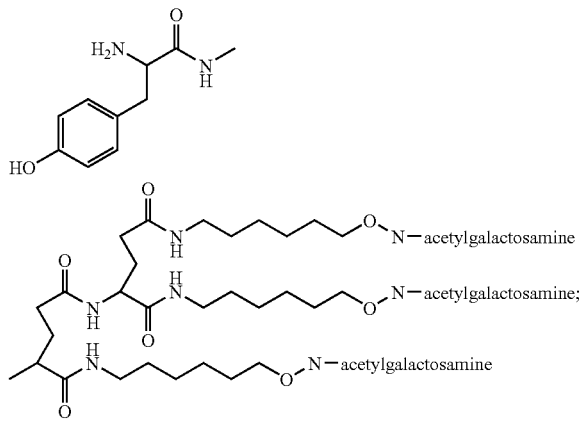

L is a bifunctional linker that is covalently bonded to A and P;
P comprises two to six 5-fluorodeoxyuridine that are linked by covalent bonds;
wherein either or both of the covalent bond between A and P and the covalent bond between L and P are biodegradable.

2. A pharmaceutical composition comprising the conjugate of claim 1 and a pharmaceutically acceptable carrier.

3. A method for treating hepatocellular carcinoma comprising administering the compound of claim 1.

* * * * *